United States Patent
Bovino et al.

(10) Patent No.: US 9,046,735 B2
(45) Date of Patent: Jun. 2, 2015

(54) METHOD AND SYSTEM FOR DETERMINING SECOND-ORDER NONLINEAR OPTICAL COEFFICIENTS

(75) Inventors: Fabio Antonio Bovino, Genoa (IT); Maria Cristina Larciprete, Rome (IT); Maurizio Giardina, Genoa (IT); Concita Sibilia, Rome (IT)

(73) Assignee: Selex Sistemi Integrati S.p.A., Roma (IT)

( * ) Notice: Subject to any disclaimer, the term of this patent is extended or adjusted under 35 U.S.C. 154(b) by 905 days.

(21) Appl. No.: 13/262,601

(22) PCT Filed: Mar. 31, 2009

(86) PCT No.: PCT/IT2009/000131
§ 371 (c)(1),
(2), (4) Date: Feb. 9, 2012

(87) PCT Pub. No.: WO2010/113190
PCT Pub. Date: Oct. 7, 2010

(65) Prior Publication Data
US 2012/0158366 A1    Jun. 21, 2012

(51) Int. Cl.
*H03F 1/26* (2006.01)
*G02F 1/35* (2006.01)
*G01N 21/21* (2006.01)
*G01N 21/41* (2006.01)
*G01N 21/63* (2006.01)

(52) U.S. Cl.
CPC .............. *G02F 1/3532* (2013.01); *G01N 21/21* (2013.01); *G01N 21/41* (2013.01); *G01N 21/636* (2013.01)

(58) Field of Classification Search
None
See application file for complete search history.

(56) References Cited

U.S. PATENT DOCUMENTS

2005/0259935 A1* 11/2005 Hamada .................. 385/129

FOREIGN PATENT DOCUMENTS

CN    101295117 A    10/2008
JP    9-166798    6/1997

OTHER PUBLICATIONS

International Search Report from corresponding PCT/IT2009/000131 dated Sep. 23, 2009.
Written Opinion in corresponding PCT/IT2009/000131 dated Sep. 23, 2009.

(Continued)

*Primary Examiner* — Aditya Bhat
(74) *Attorney, Agent, or Firm* — Marshall, Gerstein & Borun LLP

(57) ABSTRACT

Described herein is a method for determining second-order nonlinear optical coefficients of a material. The method envisages the steps of providing a specimen made at least in part of the material, causing a first optical signal and a second optical signal having, respectively, a first pulsation and a second pulsation, and a first polarization state and a second polarization state, to impinge upon the specimen in such a way that the specimen generates a second-harmonic optical signal having a third pulsation equal to the sum of the first and second pulsations, and a third polarization state that is a function of the first and second polarization states. The method further envisages the step of determining a plurality of measurements of power corresponding to the second-harmonic optical signal, and the step of determining the second-order nonlinear optical coefficients on the basis of the plurality of measurements of power. In addition, the method envisages performing a plurality of measurements of power of the second-harmonic optical signal as the first polarization state and the second polarization state vary.

22 Claims, 4 Drawing Sheets

(56) References Cited

OTHER PUBLICATIONS

International Preliminary Report on Patentability in corresponding PCT/IT2009/000131 dated Jun. 22, 2011.

Klm et al., "Improved Maker-fringe analysis for estimation of second-order nonlinearities of arrayed ZnO nanorods," Lasers and Electro-Optics, Cleo-Pacific Rim 2007 Conference on IEEE, PI, Aug. 1, 2007, pp. 1-2.

Kuwata et al., "Non-Linear Ellipsometer for the Measurement of Coherent and Incoherent Polarization Change in Optically Non-Linear Medium," Japanese Journal of Applied Physics 25(9), Sep. 1986, pp. 1382-1387.

Cattaneo et al., "Determination of second-order susceptibility components of thin films by two-beam second-harmonic generation," Optics Letters 28(16), Aug. 15, 2003, pp. 1445-1447.

Rodriguez et al., "Multipolar tensor analysis of second-order nonlinear optical response of surface and bulk of glass," Optics Express 15(14), Jul. 9, 2007, pp. 8695-8701.

First Office Action for Chinese Application No. 200980159617.5, dated Nov. 20, 2013.

\* cited by examiner

METHOD AND SYSTEM FOR DETERMINING SECOND-ORDER NONLINEAR OPTICAL COEFFICIENTS

TECHNICAL FIELD

The present invention relates to a method and to a system for determining second-order nonlinear optical coefficients.

BACKGROUND ART

As is known, when an electrical field E penetrates inside an optically linear material, it induces inside the material a polarization P, which depends upon the electrical field E and can be expressed as:

$$P = \chi^{(1)} E \quad (1)$$

where $\chi^{(1)}$ is a tensor of rank two, referred to as linear susceptivity.

In the case where the material is optically nonlinear, the polarization P depends upon powers of the electrical field E according to the following equation:

$$P = \chi^{(1)} E + \chi^{(2)} EE + \chi^{(3)} EEE + \quad (2)$$

where the coefficients $\chi^{(2)}, \chi^{(3)}$ etc. are defined as nonlinear susceptivity of the second order, third order, etc., and are tensors respectively of rank three, four, etc.; in other words, an n-order susceptivity $\chi^{(n)}$ is a tensor of rank n+1.

As is known, a particular importance is assumed by the second-order nonlinear susceptivity $\chi^{(2)}$, which is a characteristic of the materials that have a non-centrosymmetrical crystalline structure inherent in the so-called phenomenon of second-harmonic generation (SHG).

In detail, in the case where the electrical field E is oscillating with a pulsation $\omega$, and can consequently be expressed as $E = E_0 \cos(\omega t - kz)$, it is possible to show that, if the higher-order terms are neglected, the polarization P is given by the following equation:

$$P = \chi^{(1)} E_0 \cos(\omega t - kz) + \tfrac{1}{2} \chi^{(2)} E_0^2 [1 + \cos(2\omega t - 2kz)] \quad (3)$$

where evident is the presence of a component equal to $\tfrac{1}{2} \chi^{(2)} E_0^2 \cos(2\omega t - 2kz)$, which hence oscillates at a pulsation $2\omega$ that is twice the pulsation $\omega$ of the electrical field E and is responsible for the generation of a second harmonic, i.e., of the generation of an electrical field having pulsation $2\omega$ that is twice the pulsation $\omega$ of the electrical field E.

For the purposes of characterization of the materials, and in particular for the purposes of determination of the optical characteristics of a material, it is consequently of particular importance to determine the second-order nonlinear susceptivity $\chi^{(2)}$, i.e., to determine the twenty-seven elements of the corresponding tensor.

From a physical standpoint, the determination of the aforementioned twenty-seven elements amounts to the determination of a subset of mutually independent elements, the remaining elements depending upon said mutually independent elements.

In detail, designating by $\chi_{ijk}^{(2)}$ (with indices i, j, k=1, 2, 3) the elements of the second-order nonlinear susceptivity tensor $\chi^{(2)}$, it may be shown that, in the conditions where the so-called intrinsic permutation symmetry applies, i.e., assuming a stationary-state regime, the elements $\chi_{ijk}^{(2)}$ do not vary with respect to permutations of the index j and of the index k, with the consequence that the relation $\chi_{ijk}^{(2)} = \chi_{ikj}^{(2)}$ applies. Consequently, on account of the intrinsic permutation symmetry, the number of independent elements $\chi_{ijk}^{(2)}$ drops from twenty-seven to eighteen.

Recalling that the nonlinear optical properties of the materials are generally expressed in terms of the so-called second-order nonlinear optical tensor $\tilde{d}$, the elements $d_{ijk}$ of which depend upon corresponding elements $\chi_{ijk}^{(2)}$ of the second-order nonlinear susceptivity $\chi^{(2)}$ according to the equation $d_{ijk} = 0.5 \ast \chi_{ijk}^{(2)}$, the aforementioned second-order nonlinear optical tensor d may be expressed in the following contracted form:

$$\tilde{d} = \begin{pmatrix} d_{11} & d_{12} & d_{13} & d_{14} & d_{15} & d_{16} \\ d_{21} & d_{22} & d_{23} & d_{24} & d_{25} & d_{26} \\ d_{31} & d_{32} & d_{33} & d_{34} & d_{35} & d_{36} \end{pmatrix} \quad (4)$$

The form of the second-order nonlinear optical tensor $\tilde{d}$ given in eq. 4 is referred to the principal axes of the material to which the tensor $\tilde{d}$ refers, and derives from a contraction of the indices j and k based upon the intrinsic permutation symmetry. Operatively, the elements $d_{ijk}$, which are also referred to as second-order nonlinear optical coefficients, are expressed as $d_{im}$ (with i=1, 2, 3 and m=1 ... 6), which are obtained on the basis of the relations $d_{i1} = d_{i11}$, $d_{i2} = d_{i22}$, $d_{i3} = d_{i33}$, $d_{i4} = d_{i23} = d_{i32}$, $d_{i5} = d_{i13} = d_{i31}$ and $d_{i6} = d_{i12} = d_{i21}$.

In addition, it may be shown that, in the case where the conditions of symmetry of permutation of the indices (also known as Kleinman symmetry conditions) apply, i.e., in conditions of remoteness from possible resonances of the material and of negligible dispersion, where by dispersion is understood the dependence of the elements $d_{ijk}$ upon the pulsation $\omega$, the elements $d_{ijk}$ are invariant with respect to permutations of the indices i, j, k, with the consequence that the relation $d_{ijk} = d_{ikj} = d_{kji} = d_{kij} = d_{jik} = d_{jki}$ applies. There hence occurs a further reduction of the independent elements $d_{ijk}$, and hence a further reduction of the independent elements $d_{im}$.

In addition, many materials have a second-order nonlinear optical tensor $\tilde{d}$ with numerous elements $d_{im}$ that are substantially zero, on account of symmetries present in their own crystal lattices.

As is known, in order to determine the elements $d_{im}$ of the second-order nonlinear optical tensor $\tilde{d}$ for a given material, the so-called "Maker-fringe method" can be applied. The Maker-fringe method, described, for example, in the article by J. Jerphagon and S. K. Kurtz, "*Maker fringes: a detailed comparison of theory and experiment for isotropic and uniaxial crystals*", Journal of Applied Physics, Vol. 41, no. 4, pp. 1667-1681 (1970), envisages causing an optical pump signal with pulsation $\omega$ to impinge upon a surface of a specimen of said material in such a way that the specimen will generate at output a second-harmonic optical signal with pulsation $2\omega$. Next, the Maker-fringe method envisages measuring the power associated to the second-harmonic optical signal and determining the elements $d_{im}$ on the basis of said power measurements. In greater detail, if we define as "angle of inclination" the angle at which the optical pump signal impinges with respect to the normal to the surface of the specimen, the Maker-fringe method envisages measuring the power associated to the second-harmonic optical signal as the angle of inclination varies. The variation of the angle of inclination is obtained by rotation of the specimen, for example using purposely provided actuators. The power profile thus obtained exhibits oscillations (fringes), due to the interference between two electromagnetic waves generated inside the specimen and known one as "free wave" and the other as "bound wave". On the basis of said oscillations, it is possible to determine the elements $d_{im}$.

Even though the Maker-fringe method typically envisages a so-called collinear configuration of the optical pump signal and of the second-harmonic optical signal, i.e., it envisages sending a single optical pump signal onto the specimen and observing at output from the specimen a second-harmonic optical signal having approximately the same direction of propagation as the optical pump signal, a variant of the Maker-fringe method has also been proposed. According to said variant, use is envisaged of two optical pump signals, the directions of propagation of which form an angle of mutual incidence, the direction of propagation of the second-harmonic optical signal lying substantially along the bisectrix of the angle of mutual incidence. This variant of the Maker-fringe method enables higher levels of precision to be obtained.

Even though the Maker-fringe method, and the corresponding variant, have both proven effective in enabling determination of a certain number of elements $d_{im}$ of optically nonlinear materials, they both present certain drawbacks.

In particular, and with reference to the Maker-fringe method, in the case where the specimen presents a large thickness (some microns), measured in the direction of propagation of the optical pump signal, the fringes are densely distributed as a function of the angle of inclination, i.e., the aforementioned power profile presents adjacent peaks corresponding to angles of inclination that are very close to one another. In said conditions, a high angular resolution is required, understood as a high precision as the angle of inclination of the optical pump signal is varied by means of actuators. In addition, in the case where, as typically occurs, the optical pump signal is formed by laser pulses having a time duration such that the spatial extent of the pulse is comparable to or shorter than the thickness of the specimen, the variation of the angle of inclination causes the optical pump signal to interact with different portions of the specimen, with consequent possible errors in the determination of the elements $d_{im}$. In addition, in the case where the specimen is formed by a nanostructured thin film, i.e., by a film with two-dimensional or three-dimensional structural inhomogeneities, the rotation of the specimen causes, as the angle of inclination varies, the optical pump signal to interact with portions of specimen with markedly different characteristics.

As regards the non-collinear variant of Maker method, it enables determination of elements $d_{im}$ that cannot be determined using the collinear configuration, but in any case involves a rotation of the specimen, with the consequent disadvantages described above.

Two documents which relate to the determination of the second order response of centrosymmetrical materials are: "Multipolar tensor analysis of second order nonlinear optical response of surface and bulk of a glass", F. J. Rodriguez, OPTICS EXPRESS, vol. 15, no. 14, 2007-07-09, pages 8695-8701; and "Determination of second-order susceptibility components of thin films by two-beam second-harmonic generation", S. Cattaneo et al., OPTICS LETTERS of the Optical Society of America, vol. 28, no. 16, 2003-08-15, pages 1445-1447.

DISCLOSURE OF INVENTION

The aim of the present invention is to provide a method and a system for determining second-order nonlinear optical coefficients that will solve at least in part the drawbacks of the known art referred to above.

According to the present invention a method and a system for determining second-order nonlinear optical coefficients are provided, as described in Claim 1 and Claim 19, respectively.

BRIEF DESCRIPTION OF THE DRAWINGS

For a better understanding of the invention, embodiments thereof are now described, purely by way of non-limiting examples and with reference to the attached drawings, wherein.

BEST MODE FOR CARRYING OUT THE INVENTION

Figure 5:
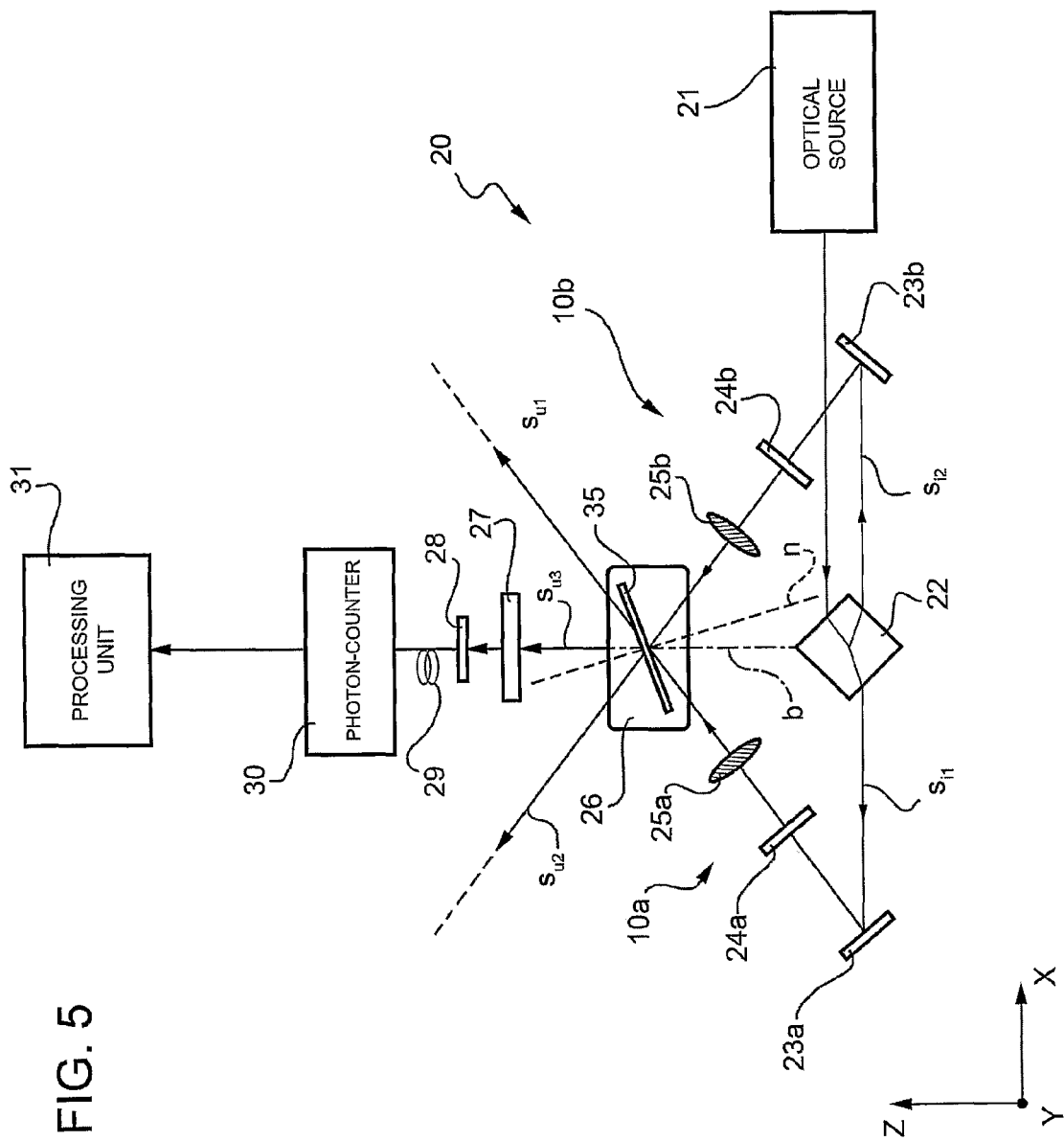
FIG. 5 shows in a schematic form a system for determining second-order nonlinear optical coefficients according to the present invention.

Given a specimen 1 (FIG. 1) made at least in part of an optically nonlinear material, i.e., having a second-order nonlinear optical tensor $\tilde{d}$ with one or more elements $d_{im}$ of non-negligible value, the present method envisages generating a second-harmonic optical signal $s_{u3}$ causing a first optical pump signal $s_{i1}$ and a second optical pump signal $s_{i2}$ to impinge upon the specimen 1, said signals having, respectively, a first pulsation $\omega_{i1}$ and a second pulsation $\omega_{i2}$, and a first polarization state and a second polarization state, which are described in detail hereinafter. In addition, the present method envisages carrying out measurements of the power associated to the second-harmonic optical signal $s_{u3}$ as the first and second polarization states vary, and determining the second-order nonlinear optical coefficients $d_{im}$ (referred to also, for reasons of brevity, as coefficients $d_{im}$) of the optically nonlinear material on the basis of said measurements. As described in greater detail hereinafter, to carry out the aforementioned measurements of power recourse is had to a system 20 for determining the coefficients $d_{im}$, an example of which is shown in FIG. 5.

Figure 1:
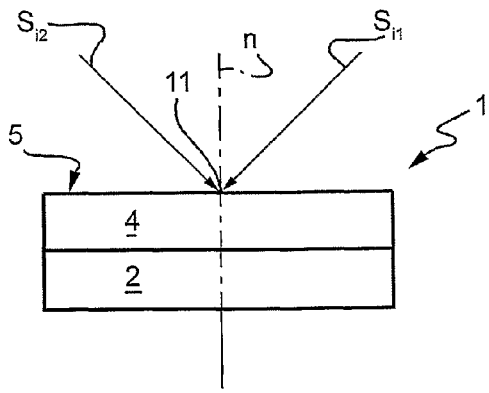
FIG. 1 shows a cross section of a specimen.

In the sequel of the present treatment it is assumed, without this implying any loss of generality, that the specimen 1 has a substantially parallelepipedal shape, as illustrated in FIG. 1. In greater detail, the specimen 1 comprises a substrate 2 (optional), for example made of sapphire ($Al_2O_3$), and a second-harmonic-generator (SHG) layer 4, set on the substrate 2 and made of the aforementioned optically nonlinear material. The substrate 2 and the second-harmonic-generator layer 4 referred to above are of a plane type, have a constant thickness, and planes of lie that are parallel to one another, thus providing a stacked stratified structure. Moreover designated by 5 in FIG. 1 is a surface of incidence, which delimits a face of the second-harmonic-generator layer 4, impinging upon which are the optical pump signals $s_{i1}$, $s_{i2}$.

Figure 2:
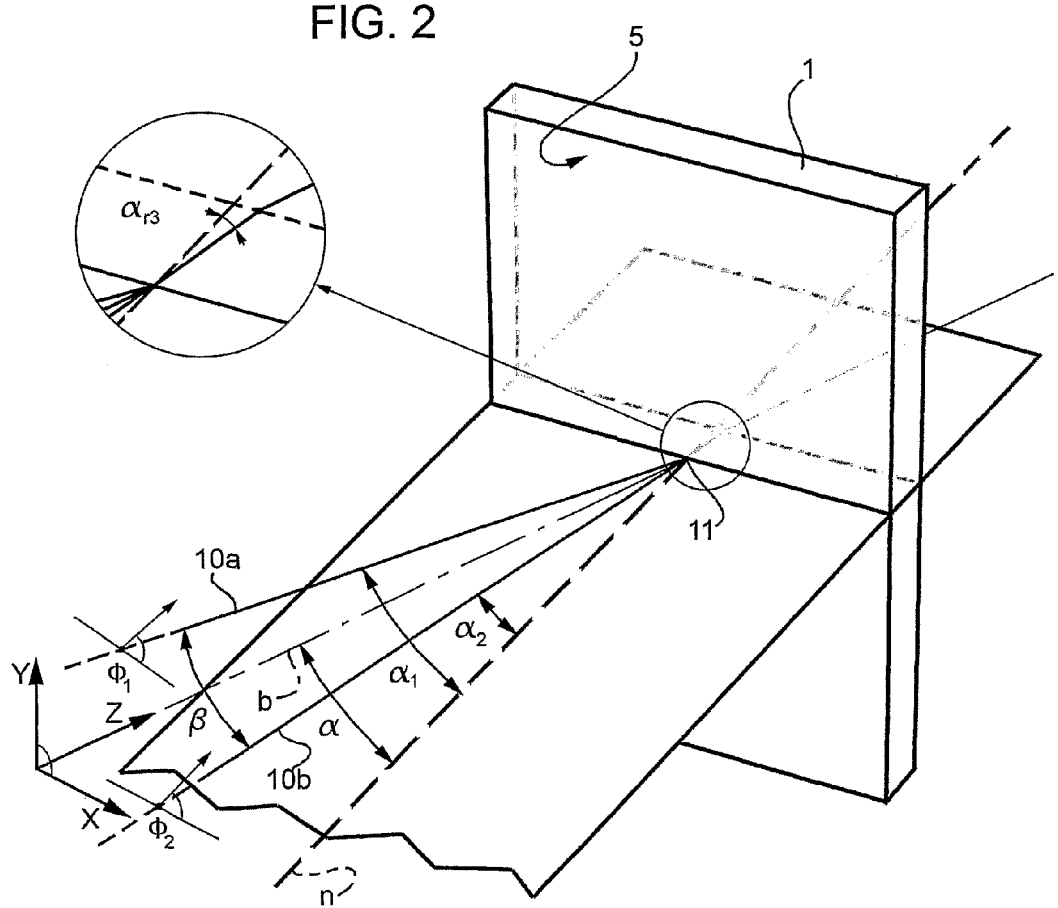
FIG. 2 shows a geometrical scheme of principle corresponding to the second-harmonic generation in the non-collinear configuration.

As is shown in FIG. 2, the first and second optical pump signals $s_{i1}$, $s_{i2}$ propagate respectively along a first optical path 10a and a second optical path 10b, which are coplanar to one another and impinge in one and the same point 11 of the surface of incidence 5, which in what follows will be referred to as point of incidence 11. In addition, the first and second optical paths 10a, 10b form between them an angle of mutual incidence β, the bisectrix b of which forms an angle of inclination α with a normal n to the surface of incidence 5 passing through the point of incidence 11. Said angle of inclination α indicates the inclination of the specimen 1 with respect to the direction identified by the bisectrix b. It should be noted, moreover, how the direction of the bisectrix b has been assumed, without this implying any loss of generality, parallel to a longitudinal axis z of a reference system used in the description of the present method and shown once again in FIG. 2. Given said reference system, the first and second optical paths 10a, 10b lie in the plane xz.

Given the angle of inclination α, the first and second optical paths 10a, 10b (hence, the optical pump signals $s_{i1}$, $s_{i2}$) impinge upon the surface of incidence 5 forming with the normal n, respectively, a first angle of incidence and a second angle of incidence, designated as $\alpha_1$ and $\alpha_2$ and equal, respectively, to α+β/2 and α−β/2. Once again without this implying any loss of generality, it is moreover assumed that, in the case where the optically nonlinear material is of a uniaxial type, the normal n is parallel to the principal optical axis of the optically nonlinear material.

From a practical standpoint, the first and second optical pump signals $s_{i1}$, $s_{i2}$ are formed by respective beams, which to a first approximation are gaussian beams. For said beams it is in any case possible to define, in a way in itself known, a first direction of propagation and a second direction of propagation, which in the case in point coincide with the first optical path 10a and the second optical path 10b, respectively.

The first and second optical pump signals $s_{i1}$, $s_{i2}$ are both linearly polarized and present, respectively, a first polarization state and a second polarization state. Since the first and second optical pump signals $s_{i1}$, $s_{i2}$ are both linearly polarized, the first and second polarization states are defined using, respectively, a first polarization angle $\phi_1$ and a second polarization angle $\phi_2$. As shown once again in FIG. 2, the first and second polarization angles $\phi_1$ and $\phi_2$ lie in planes perpendicular to the first optical path 10a and to the second optical path 10b, respectively, and are measured starting, respectively, from the intersections of said perpendicular planes with the plane xz. It follows that, approximating the first and second optical pump signals $s_{i1}$, $s_{i2}$ with corresponding plane waves, and designating, respectively, by $\vec{E}_1$ and $\vec{E}_2$ the vectors of the electrical fields associated, respectively, to the first optical pump signal $s_{i1}$ and to the second optical pump signal $s_{i2}$, it is possible to express said vectors by rendering explicit the respective (normalized) components along the axes x, y, z of the reference system shown in FIG. 2, to obtain $$\vec{E}_1 = (\sin(\phi_1) - \cos(\phi_1)\cos(\alpha_1) - \cos(\phi_1)\sin(\alpha_1))$$

$$\vec{E}_2 = (\sin(\phi_2) - \cos(\phi_2)\cos(\alpha_2) - \cos(\phi_2)\sin(\alpha_2)) \quad (5)$$

After the optical pump signals $s_{i1}$, $s_{i2}$ have impinged upon the surface of incidence 5 of the specimen 1, they are refracted and propagate inside the specimen 1, traversing in succession the second-harmonic-generator layer 4 and the substrate 2. In detail, given the first and second angles of incidence $\alpha_1$ and $\alpha_2$, the first and second optical pump signals $s_{i1}$, $s_{i2}$ propagate inside the second-harmonic-generator layer 4 forming with the normal n, respectively, a first angle of refraction $\alpha_{r1}$ and a second angle of refraction $\alpha_{r2}$, which can be determined in a way in itself known on the basis of the Snell's law and of the angles of incidence $a_1$ and $\alpha_2$.

As they propagate inside the optically nonlinear material, the first and second optical pump signals $s_{i1}$, $s_{i2}$ induce a nonlinear polarization of the optically nonlinear material, said polarization having harmonic components due to the interaction of each optical pump signal $s_{i1}$, $s_{i2}$ with itself, hence with pulsations equal to $2\omega_1$ and $2\omega_2$, respectively, and due to the mutual interaction of the first and second optical pump signals $s_{i1}$, $S_{i2}$, hence with pulsation equal to $\omega_1 + \omega_2$.

If we assume, without this implying any loss of generality, that the first and second pulsations $\omega_{i1}$, $\omega_{i2}$ of the first and second optical pump signals $s_{i1}$, $s_{i2}$ are the same as one another and equal to $\omega_i$, it is found that at output from the specimen 1, in addition to the optical pump signals $s_{i1}$, $s_{i2}$, three second-harmonic optical signals $s_{u1}$, $s_{u2}$ and $s_{u3}$ are present, which are also linearly polarized and which have, respectively, pulsations $\omega_{u1}$, $\omega_{u2}$ and $\omega_{u3}$, all equal to $2\omega_i$.

The second-harmonic optical signals $s_{u1}$ and $s_{u2}$ have wave vectors $\vec{k}_{u1}$ and $\vec{k}_{u2}$, with directions approximately collinear to the directions of the wave vectors of the optical pump signals $s_{i1}$, $s_{i2}$ at input to the specimen 1. Instead, the second-harmonic optical signal $s_{u3}$ has a wave vector $\vec{k}_{u3}$ directed, to a first approximation, along the axis z, irrespective of the angle of inclination α. In greater detail, the second-harmonic optical signal $s_{u3}$ propagates inside the second-harmonic-generator layer 4 in such a way that the wave vector $\vec{k}_{u3}$ forms with the normal n a third angle of refraction $\alpha_{r3}$. Said angle of refraction $\alpha_{r3}$ can be determined in a way in itself known on the basis of the law of conservation of the tangential components of the wave vectors, i.e., on the basis of the equation $\vec{k}_{u1} \sin(\alpha_{r1}) + \vec{k}_{u2} \sin(\alpha_{r2}) = k_{u3}^x$. As described in greater detail hereinafter, the generation of second-harmonic optical signals depends upon the angles of incidence $\alpha_1$ and $\alpha_2$ and upon the polarization of the first and second optical pump signals $s_{i1}$, $s_{i2}$. In particular, it is found that it is possible to vary the polarization of the second-harmonic optical signal $s_{u3}$ by acting on the polarizations of the first and second optical pump signals $s_{i1}$, $s_{i2}$, hence by varying the first and second polarization angles $\phi_1$ and $\phi_2$.

In detail, each of the aforementioned optical signals, both the pump signals $s_{i1}$, $s_{i2}$ and the second-harmonic signal $s_{u3}$, can be decomposed, in so far as they are linearly polarized, into two components which have linear polarizations that are orthogonal to one another (i.e., they have directions of polarization that are mutually orthogonal) and which in what follows will be referred to as component P and component S. In particular, and with reference to FIG. 2, the component P of each of the aforementioned optical signals $s_{i1}$, $s_{i2}$, $s_{u3}$ is the component the electrical field of which lies in the plane xz (i.e., with polarization angle $\phi_i = 0$), whilst the component S is the component the electrical field of which lies in the plane xy (i.e., with polarization angle $\phi_i = 90°$. In what follows, the components P of the optical pump signals $s_{i1}$, $s_{i2}$ and of the second-harmonic optical signal $s_{u3}$ will be referred to as components $Ps_{i1}$, $Ps_{i2}$, $Ps_{u3}$, respectively. Likewise, the corresponding components S will be referred to as components $Ss_{i1}$, $Ss_{i2}$, $Ss_{u3}$, respectively. In addition, in what follows referred to as polarized optical signals P or S are optical signals comprising just the component P or just the component S.

By way of example, it should be noted how, on the basis of the angle $\alpha_{r3}$, it is possible to express the (normalized) components corresponding to the axes x, y, z of the component $Ss_{u3}$ and of the component $Ps_{u3}$ of the second-harmonic optical signal $s_{u3}$ as (1 0 0) and $(0 -\cos(\alpha_{r3}) -\sin(\alpha_{r3}))$, respectively.

Operatively, once the angle of inclination $\alpha$ and the angle of mutual incidence $\beta$ have been fixed, by varying the polarizations of the first and second optical pump signals $s_{i1}$, $s_{i2}$ (i.e., by varying the first and second polarization angles $\phi_1$ and $\phi_2$) it is possible to vary the power associated to the component $Ps_{u3}$ and to the component $Ss_{u3}$ of the second-harmonic optical signal $s_{u3}$ at output from the specimen 1.

The distribution of the power between the component $Ps_{u3}$ and the component $Ss_{u3}$ of the second-harmonic optical signal $s_{u3}$ depends upon the crystalline structure of the optically nonlinear material. Consequently, by measuring the power associated to the component $Ps_{u3}$ and to the component $Ss_{u3}$ of the second-harmonic optical signal $s_{u3}$, it is possible to determine the second-order nonlinear optical coefficients $d_{im}$. In detail, if we designate by $W_{i1}$ and $W_{i2}$ the powers associated to the first optical pump signal $s_{i1}$ and to the second optical pump signal $s_{i2}$, respectively, it may be shown that the powers $W_{u3}^P$ and $W_{u3}^s$ associated, respectively, to the component $Ps_{u3}$ and to the component $Ss_{u3}$ of the second-harmonic optical signal $s_{u3}$, are given by $$W_{u3}^S(\alpha) = \left(\frac{512\pi^3}{A_1 \cdot A_2}\right) \cdot (t_{i1}^{\phi_1})^2 \cdot (t_{i2}^{\phi_2})^2 \cdot T_{2\omega_i}^S \cdot W_{i1} \cdot \tag{6}$$

$$W_{i2} \cdot \frac{\sin^2(\Psi_{SHG}^{\phi_1\phi_2 \to S}(\alpha))}{[n_{i1}^{\phi_1}(\omega_i) \cdot n_{i2}^{\phi_2}(\omega_i) - n_{u3}^S(2\omega_i)^2]^2} \left(d_{eff}^{\phi_1\phi_2 \to S}(\alpha)\right)^2$$

$$W_{u3}^P(\alpha) = \left(\frac{512\pi^3}{A_1 \cdot A_2}\right) \cdot (t_{i1}^{\phi_1})^2 \cdot (t_{i2}^{\phi_2})^2 \cdot T_{2\omega_i}^P \cdot W_{i1} \cdot \tag{7}$$

$$W_{i2} \cdot \cdot \frac{\sin^2(\Psi_{SHG}^{\phi_1\phi_2 \to P}(\alpha))}{[n_{i1}^{\phi_1}(\omega_i) \cdot n_{i2}^{\phi_2}(\omega_i) - n_{u3}^P(2\omega_i)^2]^2} \left(d_{eff}^{\phi_1\phi_2 \to P}(\alpha)\right)^2$$

where:
  $A_1$ and $A_2$ are transverse areas defined by the intersection of the optical pump signals $s_{i1}$ and $s_{i2}$ (or rather, by the corresponding beams) with the surface of incidence 5;
  $t_{i1}^{\phi_1}$ and $t_{i2}^{\phi_2}$ the Fresnel transmission coefficients for the electrical fields of the optical pump signals $s_{i1}$ and $s_{i21}$ at the interface between the air and the specimen 1, and depend, respectively, upon the first polarization angle $\phi_1$ and upon the second polarization angle $\phi_2$;
  $T_{2\omega_i}^S$ and $T_{2\omega_i}^P$ are the Fresnel transmission coefficients for the intensity of the second-harmonic optical signal $s_{u3}$ at output from the specimen, i.e., at the interface between the substrate 2 and the air, in the case of a second-harmonic optical signal $s_{u3}$ with S polarization or P polarization, respectively;
  $n_{i1}^{\phi_1}(\omega_i)$ and $n_{i2}^{\phi_2}(\omega_i)$ are the refractive indices of the optically nonlinear material for the first optical pump signal $s_{i1}$ and the second optical pump signal $s_{i2}$, respectively; $n_{i1}^{\phi_1}(\omega_i)$ and $n_{i2}^{\phi_2}(\omega_i)$ are functions of the pulsation $\omega_i$ and, respectively, of the first angle of refraction $\alpha_{r1}$ and of the first polarization angle $\phi_1$, and of the second angle of refraction $\alpha_{r2}$ and of the second polarization angle $\phi_2$;
  $n_{u3}^S(2\omega_i)$ and $n_{u3}^P(2\omega_i)$ are the refractive indices of the optically nonlinear material, respectively for the component $Ss_{u3}$ and the component $Ps_{u3}$ of the second-harmonic optical signal $s_{u3}$, are functions of the first and second angles of refraction $\alpha_{r1}$, $\alpha_{r2}$, and can be determined, in a way in itself known, on the basis of the so-called ellipsoid of the indices of the optically nonlinear material;

$d_{eff}^{\phi_1\phi_2 \to S}(\alpha)$ and $d_{eff}^{\phi_1\phi_2 \to P}(\alpha)$ are effective nonlinear optical coefficients, described in greater detail hereinafter and corresponding, respectively, to the component $Ss_{u3}$ and to the component $Ps_{u3}$ of the second-harmonic optical signal $s_{u3}$; both of the effective nonlinear optical coefficients depend upon the first and second angles of refraction $\alpha_{r1}$ and $\alpha_{r2}$, as well as upon the first and second polarization angles $\phi_1$ and $\phi_2$;
  $\Psi_{SHG}^{\phi_1\phi_2 \to S}(\alpha)$ and $\Psi_{SHG}^{\phi_1\phi_2 \to P}(\alpha)$ are phase factors, described in greater detail hereinafter and corresponding, respectively, to the component $Ss_{u3}$ and to the component $Ps_{u3}$; both of the phase factors depend upon the first and second angles of refraction $\alpha_{r1}$ and $\alpha_{r2}$, as well as upon the first and second polarization angles $\phi_1$ and $\phi_2$.

In greater detail, the phase factors $\Psi_{SHG}^{\phi_1\phi_2 \to S}(\alpha)$ and $\Psi_{SHG}^{\phi_1\phi_2 \to P}(\alpha)$ are given by the following equations:

$$\Psi_{SHG}^{\phi_1\phi_2 \to P}(\alpha) = \tag{8}$$
$$\left(\frac{\pi L}{2}\right)\left(\frac{2}{\lambda}\right)\left[n_{i1}^{\phi_1}(\omega_i) \cdot \cos(\alpha_{r1}) + n_{i2}^{\phi_2}(\omega_i) \cdot \cos(\alpha_{r2}) - 2n_{u3}^S(2\omega_i) \cdot \cos(\alpha_{r3})\right]$$

$$\Psi_{SHG}^{\phi_1\phi_2 \to P}(\alpha) = \tag{9}$$
$$\left(\frac{\pi L}{2}\right)\left(\frac{2}{\lambda}\right)\left[n_{i1}^{\phi_1}(\omega_i) \cdot \cos(\alpha_{r1}) + n_{i2}^{\phi_2}(\omega_i) \cdot \cos(\alpha_{r2}) - 2n_{u3}^P(2\omega_i) \cdot \cos(\alpha_{r3})\right]$$

where:
  L is the thickness of the second-harmonic-generator layer 4;
  $\lambda$ is the wavelength of the optical pump signals $s_{i1}$ and $s_{i2}$ in a vacuum;
  $\alpha_{r1}$, $\alpha_{r2}$ are the aforesaid first and second angles of refraction, corresponding, respectively, to the first and second optical pump signals $s_{i1}$ and $s_{i2}$; and
  $\alpha_{r3}$ is the aforesaid third angle of refraction, corresponding to the second-harmonic optical signal $s_{u3}$, and to a first approximation is equal to the angle of incidence $\alpha$.

As regards the effective nonlinear optical coefficients $d_{eff}^{\phi_1\phi_2 \to S}(\alpha)$ and $d_{eff}^{\phi_1\phi_2 \to P}(\alpha)$, also referred to in brief as effective coefficients $d_{eff}^{\phi_1\phi_2 \to S}(\alpha)$ and $d_{eff}^{\phi_1\phi_2 \to P}(\alpha)$, they depend not only upon the first, second, and third angles of refraction $\alpha_{r1}$, $\alpha_{r2}$, $\alpha_{r3}$ but also upon the second-order nonlinear optical coefficients $d_{im}$ of the optically nonlinear material, and moreover upon the polarizations of the first and second optical pump signals $s_{i1}$ and $s_{i2}$, i.e., upon the first and second polarization angles $\phi_1$ and $\phi_2$. In particular, assuming that the optically nonlinear material has a second-order nonlinear optical tensor $\bar{d}$ with all the elements $d_{im}$ different from zero and independent (eq. 4), it may be shown that the effective coefficients $d_{eff}^{\phi_1\phi_2 \to S}(\alpha)$ and $d_{eff}^{\phi_1\phi_2 \to P}(\alpha)$ are given by the following expressions:

$$d_{eff}^{\phi_1\phi_2 \to S} = (1\ 0\ 0)\begin{pmatrix} d_{11} & d_{12} & d_{13} & d_{14} & d_{15} & d_{16} \\ d_{21} & d_{22} & d_{23} & d_{24} & d_{25} & d_{26} \\ d_{31} & d_{32} & d_{33} & d_{34} & d_{35} & d_{36} \end{pmatrix} \tag{10}$$

$$\begin{pmatrix} \sin(\phi_1)\sin(\phi_2) \\ \cos(\phi_1)\cos(\alpha_{r1})\cos(\phi_2)\cos(\alpha_{r2}) \\ \cos(\phi_1)\sin(\alpha_{r1})\cos(\phi_2)\sin(\alpha_{r2}) \\ \cos(\phi_1)\cos(\phi_2)[\cos(\alpha_{r1})\sin(\alpha_{r2}) + \sin(\alpha_{r1})\cos(\alpha_{r2})] \\ -\sin(\phi_1)\cos(\phi_2)\sin(\alpha_{r2}) - \sin(\phi_2)\cos(\phi_1)\sin(\alpha_{r1}) \\ -\sin(\phi_1)\cos(\phi_2)\cos(\alpha_{r2}) - \sin(\phi_2)\cos(\phi_1)\cos(\alpha_{r1}) \end{pmatrix}$$

-continued $$d_{eff}^{\phi1\phi2\to P} = (0 \quad -\cos(\alpha_{r3}) \quad -\sin(\alpha_{r3})) \begin{pmatrix} d_{11} & d_{12} & d_{13} & d_{14} & d_{15} & d_{16} \\ d_{21} & d_{22} & d_{23} & d_{24} & d_{25} & d_{26} \\ d_{31} & d_{32} & d_{33} & d_{34} & d_{35} & d_{36} \end{pmatrix} \quad (11)$$

$$\begin{pmatrix} \sin(\phi_1)\sin(\phi_2) \\ \cos(\phi_1)\cos(\alpha_{r1})\cos(\phi_2)\cos(\alpha_{r2}) \\ \cos(\phi_1)\sin(\alpha_{r1})\cos(\phi_2)\sin(\alpha_{r2}) \\ \cos(\phi_1)\cos(\phi_2)[\cos(\alpha_{r1})\sin(\alpha_{r2}) + \sin(\alpha_{r1})\cos(\alpha_{r2})] \\ -\sin(\phi_1)\cos(\phi_2)\sin(\alpha_{r2}) - \sin(\phi_2)\cos(\phi_1)\sin(\alpha_{r1}) \\ -\sin(\phi_1)\cos(\phi_2)\cos(\alpha_{r2}) - \sin(\phi_2)\cos(\phi_1)\cos(\alpha_{r1}) \end{pmatrix}$$

Since the quantities A, $t_{i1}^{\phi1}$, $t_{i2}^{\phi2}$, $T_{2\omega_i}^{P}$, $T_{2\omega_i}^{S}$, $n_{i1}^{\phi1}(\omega_i)$, $n_{i2}^{\phi2}(\omega_i)$, $n_{u3}^{S}(2\omega_i)$, $n_{u3}^{P}(2\omega_i)$, $\Psi_{SHG}^{\phi1\phi2\to S}(\alpha)$ and $\Psi_{SHG}^{\phi1\phi2\to P}(\alpha)$ can be determined in a way in itself known, it is possible to make measurements aimed at determining the powers $W_{u3}^{P}$ and $W_{u3}^{S}$ associated, respectively, to the component $Ps_{u3}$ and to the component $Ss_{u3}$ of the second-harmonic optical signal $s_{u3}$, and then apply eqs. (6) and (7) (inside which the expressions 10 and 11 are, respectively, used) in order to determine the coefficients $d_{im}$, which represent corresponding unknowns to be determined, provided that the powers $W_{i1}$ and $W_{i2}$ have been previously determined. In this connection, it should be noted that the aforementioned measurements aimed at determining the powers $W_{u3}^{P}$ and $W_{u3}^{S}$ are carried out by means of a system 20 for determining the coefficients $d_{im}$ that is designed to implement the geometry shown in FIG. 2, an example of which is described in detail hereinafter. Consequently, the powers $W_{i1}$ and $W_{i2}$ depend upon the system 20 adopted for determining the coefficients $d_{im}$.

The determination of the powers $W_{i1}$ and $W_{i2}$, or rather of the product $W_{i1}*W_{i2}$, envisages carrying out preliminary measurements of the powers $W_{u3}^{P}$ and $W_{u3}^{S}$ associated, respectively, to the component $Ps_{u3}$ and to the component $Ss_{u3}$ of the second-harmonic optical signal $s_{u3}$ generated by a reference specimen. In detail, given the system 20 for determining the coefficients $d_{im}$, which is to be used also for the aforementioned measurements of the powers $W_{u3}^{P}$ and $W_{u3}^{S}$, in order to determine the product $W_{i1}*W_{i2}$ it is possible to provide within the determination system 20 a reference specimen (not shown), formed by a reference crystal (for example, quartz or KDP), of which the second-order nonlinear coefficients $d_{im}$ are known, and of which the effective coefficients $d_{eff}^{\phi1\phi2\to S}(\alpha)$ and $d_{eff}^{\phi1\phi2\to P}(\alpha)$ are consequently known (see expression 10 and 11).

Next, a number of preliminary measurements is performed, which are aimed at determining, for example, the power $W_{u3}^{S}$ (similar considerations apply in the case where measurements of the power $W_{u3}^{P}$ are made). Having available said preliminary power measurements and the effective coefficient $d_{eff}^{\phi1\phi2\to S}(\alpha)$, it is hence possible to determine, by means of eq. (6) and in a way in itself known (for example, applying the least-squares method), the unknown $W_{i1}*W_{i2}$. It should be noted that the aforementioned preliminary measurements are obtained in preliminary measurement conditions, i.e., for a preliminary angle of inclination $\alpha$ and a preliminary angle of mutual incidence $\beta$, and are moreover obtained preferably by assigning a fixed value to one of the two angles of polarization $\phi_1$ and $\phi_2$, and varying the other. It may moreover be noted that the effective coefficient $d_{eff}^{\phi1\phi2\to S}(\alpha)$ used in eq. (6) (equivalently, the effective coefficient $d_{eff}^{\phi1\phi2P}(\alpha)$, in the case of preliminary measurements of the power $W_{u3}^{P}$) depends not only upon the coefficients $d_{im}$ (which are known) of the reference material but also upon the angles of refraction $\alpha_{r1}$, $\alpha_{r2}$, and upon the first and second polarization angles $\phi_1$ and $\phi_2$.

In what follows, the operations described the purpose of which is to determine the product $W_{i1}*W_{i2}$ will be referred to as operations of preliminary calibration.

Once the product $W_{i1}*W_{i2}$ has been determined, it is possible to determine the (unknown) coefficients $d_{im}$ of the optically nonlinear material. In detail, in the case where the second-order nonlinear optical tensor $\bar{d}$ of the optically nonlinear material has all its elements $d_{im}$ independent, the unknowns to be determined are eighteen. However, it is possible to reduce the number of unknowns on the basis of the form of the second-order nonlinear optical tensor $\bar{d}$, where understood as "form of a tensor" is the distribution, inside the tensor, of the non-zero elements $d_{im}$; said form is characteristic of the crystalline class to which the optically nonlinear material belongs, as described, for example, in "Handbook of nonlinear optics", by R. L. Sutherland, published by Marcel Dekker Inc., New York (1996). In general, the second-order nonlinear optical tensors $\bar{d}$ of the principal crystalline classes are sparse, i.e., they have a limited number of non-zero elements $d_{im}$, with consequent reduction of the unknowns. In addition, in some cases it is possible to set to zero one or more elements $d_{im}$, in the case where it is known that they have negligible values as compared to others.

The number of unknowns can be further reduced on the basis of the Kleinman symmetry rules. In addition, on the basis of the expressions (10) and (11) it is evident that, for given values of the first polarization angle $\phi_1$ and/or of the second polarization angle $\phi_2$, as well as, possibly, for given values of the angle of refraction $\alpha_{r3}$, some contributions (addenda) of the effective coefficients $d_{eff}^{\phi1\phi2\to S}(\alpha)$ and $d_{eff}^{\phi1\phi2\to P}(\alpha)$ vanish, in such a way that the effective coefficients $d_{eff}^{\phi1\phi2\to S}(\alpha)$ and $d_{eff}^{\phi1\phi2\to P}(\alpha)$ depend upon an progressively smaller number of elements $d_{im}$.

By way of example, to illustrate the reduction in the number of unknowns, the application of the present method is described in the case of optically nonlinear material belonging to the 6 mm crystalline class. In particular, as example of material of the 6 mm crystalline class monocrystalline gallium nitride (GaN) is adopted. Once again by way of example, it is assumed that the substrate 2 is made of sapphire and that the second-harmonic-generator layer 4, consisting precisely of gallium nitride, is set above the plane c (0001) of the sapphire substrate 2. In addition, it is assumed that the second-harmonic-generator layer 4 presents a principal optical axis set in a direction perpendicular to the second-harmonic-generator layer 4, hence parallel to the normal n.

Monocrystalline gallium nitride has a crystalline structure of a wurtzite type, with a non-centrosymmetrical hexagonal elementary cell, with 6 mm point-group symmetry. In addition, gallium nitride has a second-order nonlinear optical tensor $\bar{d}$ having a form, when referred to the principal axes, of the type $$\bar{d} = \begin{pmatrix} 0 & 0 & 0 & 0 & d_{15} & 0 \\ 0 & 0 & 0 & d_{24} & 0 & 0 \\ d_{31} & d_{32} & d_{33} & 0 & 0 & 0 \end{pmatrix} \quad (12)$$

In addition, from a quantitative standpoint the relations $d_{15}=d_{24}$ and $d_{31}=d_{32}$ generally apply. Consequently, the effective coefficients $d_{eff}^{\phi1\phi2\to S}(\alpha)$ and $d_{eff}^{\phi1\phi2\to P}(\alpha)$, the general expressions of which are given by eqs. (10) and (11), assume the following simplified forms:

$$d_{\mathit{eff}}^{\phi1\phi2\to S}(\alpha)=-d_{15}(\sin(\phi_1)\cos(\phi_2)\sin(\alpha_{r2})+\cos(\phi_1)\sin(\alpha_{r1})\sin(\phi_2)) \quad (13)$$

$$\begin{aligned}d_{\mathit{eff}}^{\phi1\phi2\to P}(\alpha)=&-d_{15}\cos(\alpha_{r3})\cos(\phi_1)\cos(\phi_2)[\cos(\alpha_{r1})\\&\sin(\alpha_{r2})+\sin(\alpha_{r1})\cos(\alpha_{r2})]+-d_{31}[\sin(\alpha_{r3})\sin(\phi_1)\\&\sin(\phi_2)+\sin(\alpha_{r3})\cos(\phi_1)\cos(\alpha_{r1})\cos(\phi_2)\cos\\&(\alpha_{r2})]+-d_{33}\sin(\alpha_{r3})\cos(\phi_1)\sin(\alpha_{r1})\cos(\phi_2)\sin\\&(\alpha_{r2})\end{aligned} \quad (14)$$

On the basis of the expressions (13) and (14), the number of coefficients $d_{im}$ to be determined reduces from eighteen to three (the coefficients $d_{15}$, $d_{31}$, $d_{33}$). Assuming, as has been said previously, that the quantities $A_1$, $A_2$, $t_{i1}^{\phi1}$, $t_{i2}^{\phi2}$, $T_{2\omega_i}^P$, $T_{2\omega_i}^S$, $n_{i1}^{\phi1}(\omega_i)$, $n_{i2}^{\phi2}(\omega_i)$, $n_{u3}^S(2\omega_i)$, $n_{u3}^P(2\omega_i)$, $\Psi_{SHG}^{\phi1\phi2\to S}(\alpha)$, $\Psi_{SHG}^{\phi1\phi2\to P}(\alpha)$, and the product $W_{i1}*W_{i2}$ are known, it is possible to determine the coefficients $d_{15}$, $d_{31}$, $d_{33}$ on the basis of measurements of power of the components $Ss_{u3}$ and $Ps_{u3}$ of the second-harmonic optical signal $s_{u3}$.

In detail, first measurement conditions are established, i.e., a first angle of inclination α and a first angle of mutual incidence β, which are preferably equal, respectively, to the preliminary angle of inclination α and to the preliminary angle of mutual incidence β used during the operations of preliminary calibration. Consequently, also the first, second, and third angles of refraction $\alpha_{r1}$, $\alpha_{r2}$, $\alpha_{r3}$ are established.

Next, a first plurality of measurements is performed, aimed at determining the power $W_{u3}^S$ associated to the component $Ss_{u3}$ of the second-harmonic optical signal $s_{u3}$, each measurement being obtained for a corresponding pair of values of the first and second polarization angles $\phi_1$ and $\phi_2$. Next, second measurement conditions are established, i.e., a second angle of inclination α and a second angle of mutual incidence β, which are preferably equal to the aforementioned first measurement conditions, and a second plurality of measurements is performed, aimed at determining the power $W_{u3}^P$ associated to the component $Ps_{u3}$ of the second-harmonic optical signal $s_{u3}$, each measurement being obtained for a corresponding pair of values of the first and second polarization angles $\phi_1$ and $\phi_2$.

In other words, the components $Ss_{u3}$ and $Ps_{u3}$ of the second-harmonic optical signal $s_{u3}$ are considered separately, and, for each of said components, a cross scanning is performed, within given intervals, of the first and second polarization angles $\phi_1$ and $\phi_2$, thus determining a corresponding experimental map, which highlights the evolution of the power ($W_{u3}^S$ or $W_{u3}^P$) associated to the component considered ($Ss_{u3}$ or $Ps_{u3}$) as a function of the angles of polarization $\phi_1$ and $\phi_2$.

Operatively, the greater the number of the measurements that make up each experimental map, the higher the precision with which it is possible to determine the coefficients $d_{im}$.

On the basis of the operations described, two experimental maps are hence available, which in what follows are also referred to as experimental map S and experimental map P, according to the component ($Ss_{u3}$ or $Ps_{u3}$) of the second-harmonic optical signal $s_{u3}$ to which each map refers.

Figure 3A:
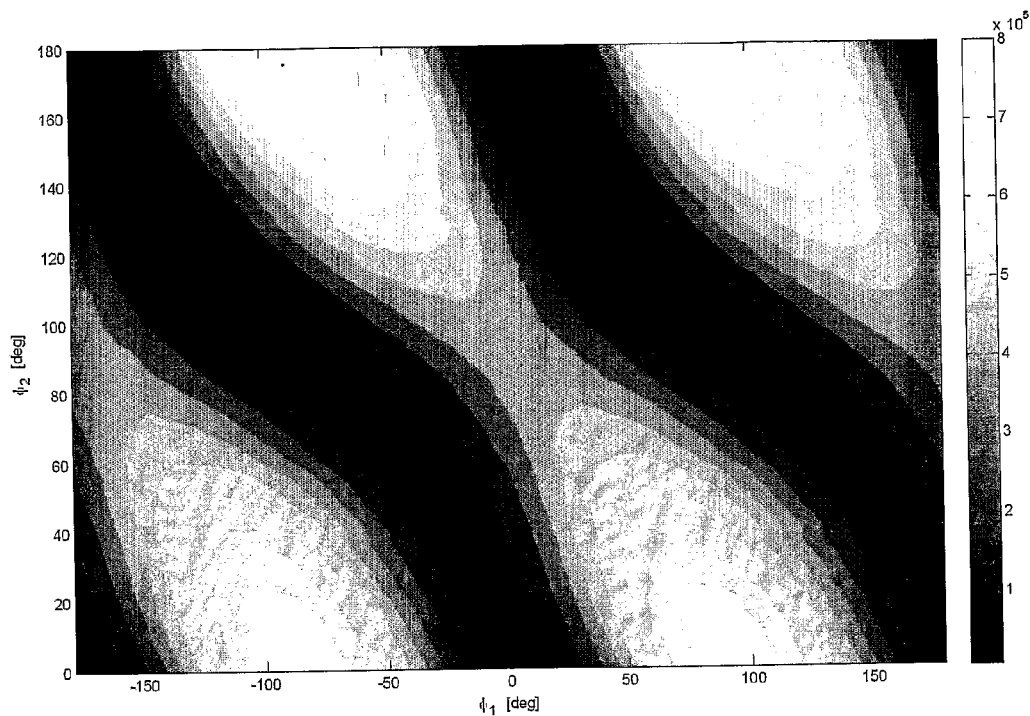
FIGS. 3a and 4a show maps of experimental measurements of power according to the present invention, corresponding, respectively, to a first component and a second component of a second-harmonic signal as a function of a first angle and of a second angle.
Figure 4A:
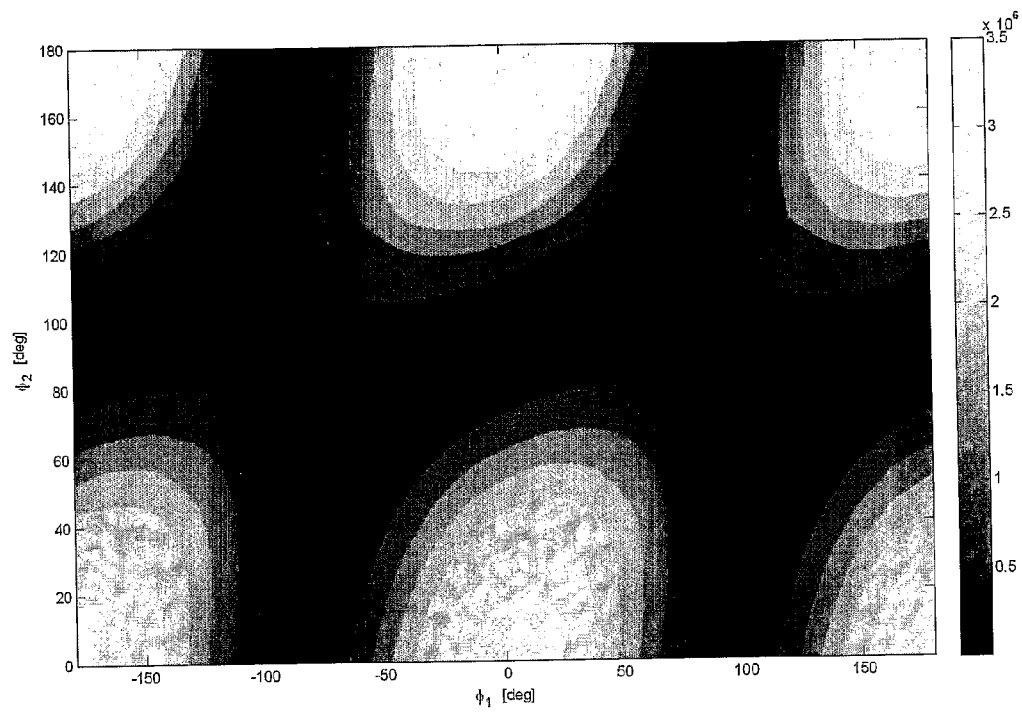

By way of example, FIGS. 3a and 4a show, respectively, an experimental map S and an experimental map P, which were obtained with an angle of inclination α of 35° and an angle of mutual incidence β of 18°. In addition, both of the maps were obtained by scanning the first polarization angle $\phi_1$ within an interval comprised between −180° and 180°, with steps of 4°, and by scanning the second polarization angle $\phi_2$ within an interval comprised between 0° and 180°, with steps of 4°. The measurements are expressed in photons per second.

On the basis of the experimental map S, of eq. (6), and of the expression (13), it is possible to determine the coefficient $d_{15}$.

In particular, it is possible to apply, in a way in itself known, the least-squares method to the measurements of the power $W_{u3}^S$ of which the experimental map S is made up in such a way as to determine a value of the coefficient $d_{15}$ that minimizes the mean square deviation between the measurements of the power $W_{u3}^S$ of the experimental map S and corresponding values yielded by eq. (6), when the effective coefficient $d_{\mathit{eff}}^{\phi1\phi2\to S}(\alpha)$ has the expression of eq. (13).

In detail, each measurement of the experimental map S corresponds to a given pair of values assumed by the first and second polarization angles $\phi_1$, $\phi_2$, and moreover all the measurements of the experimental map S have been obtained in the aforementioned first measurement conditions. Consequently, the least-squares method enables determination of a value corresponding to the coefficient $d_{15}$ such that a minimum value is obtained for the square deviation present, on average, between each measurement of the experimental map S and a corresponding value given by eq. (6), in the case in point the value of power $W_{u3}^S$ given by eq. (6) when calculated for said first measurement conditions (i.e., for the first angle of inclination α and the first angle of mutual incidence β), for said given pair of values assumed by the first and second polarization angles $\phi_1$, $\phi_2$, and moreover assigning to $d_{15}$ said value corresponding to the coefficient $d_{15}$.

Next, a first subset of measurements is selected, comprising the measurements of power $W_{u3}^P$ of the experimental map P which have been obtained with the first polarization angle $\phi_1$ of 90°, in such a way that it is legitimate to assume for the effective coefficient $d_{\mathit{eff}}^{\phi1\phi2\to P}(\alpha)$ the following expression:

$$d_{\mathit{eff}}^{\phi1\phi2\to P}(\alpha)=-d_{31}\sin(\alpha_{r3})\sin(\phi_2) \quad (15)$$

It is then possible to apply, in a way similar to what has been described as regards the coefficient $d_{15}$, the least-squares method to the measurements of the first subset of measurements so as to determine a value of the coefficient $d_{31}$ that will minimize the mean square deviation between the measurements of the power $W_{u3}^P$ of the first subset of measurements and the values yielded by eq. (7), when the effective coefficient $d_{\mathit{eff}}^{\phi1\phi2\to P}(\alpha)$ has the expression of eq. (15).

Once the coefficients $d_{15}$ and $d_{31}$ have been determined, it is possible to use the values determined for the coefficients $d_{15}$ and $d_{31}$ in order to determine the coefficient $d_{33}$. For this purpose, the least-squares method is applied to the measurements of the experimental map P so as to determine a value corresponding to the coefficient $d_{33}$ that will minimize the mean square deviation between the measurements of the power $W_{u3}^P$ of the experimental map P and the values yielded by eq. (7) when the effective coefficient $d_{\mathit{eff}}^{\phi1\phi2\to P}(\alpha)$ has the expression of eq. (14), and where the values corresponding to the coefficients $d_{15}$ and $d_{31}$ determined previously are used. In this way, all the non-zero coefficients $d_{im}$ of the second-order nonlinear optical tensor $\tilde{d}$ are determined, given that the relations $d_{15}=d_{24}$ and $d_{31}=d_{32}$ apply.

It may moreover be noted that, in the case where the gallium nitride of the specimen 1 respects the Kleinman symmetry conditions, the relations $d_{15}=d_{24}=d_{31}=d_{32}=d_{33}/2$ moreover apply. Consequently, the determination of the non-zero coefficients $d_{im}$ of the second-order nonlinear optical tensor $\tilde{d}$ reduces to the determination of just the coefficient $d_{15}$. It follows that, in the case where it is legitimate to assume a priori that the Kleinman symmetry conditions are respected, the experimental map S alone is sufficient. It should be noted, however, that the determination, not of the coefficient $d_{15}$ alone, but rather also of the coefficients $d_{31}$ and $d_{33}$, makes it possible to verify a posteriori and quantitatively whether the Kleinman symmetry conditions are respected. In fact, in the case where the values determined for the coefficients $d_{15}$, $d_{31}$, $d_{33}$ do not substantially respect the relation $d_{15}=d_{31}=-d_{33}/2$ (considering the inevitable imprecisions of the measurements and the numeric tolerances associated to the least-squares method), it is legitimate to infer that the Kleinman symmetry conditions are not respected. This can occur, for example, on account of mechanical stresses within the specimen 1, or else on account of a faulty fabrication of the specimen 1 itself.

In addition to enabling determination of the coefficients $d_{im}$, the experimental maps enable extraction of qualitative information on the crystalline structure of the optically nonlinear material of which the specimen 1 is made. Before describing further uses of the experimental maps, it is, however, expedient to describe in greater detail the experimental maps themselves, for example, with reference to the experimental map S and to the experimental map P which are shown, respectively, in FIGS. 3a and 4α.

As is shown in FIG. 3a, the power $W_{u3}^S$ associated to the component $Ss_{u3}$ of the second-harmonic optical signal $s_{u3}$ has maxima at $\phi_1=90°$, $\phi_2=0°$ (absolute maxima) and at $\phi_1=0°$, $\phi_2=90°$ (relative maxima), i.e., when the first and second optical pump signals $s_{i1}$, $s_{i2}$ have polarizations perpendicular to one another, and minima at $\phi_1=\phi_2=0°$ and $\phi_1=\phi_2=90°$, i.e., when the first and second optical pump signals $s_{i1}$, $s_{i2}$ have parallel polarizations.

As shown, instead, in FIG. 4a, the power $W_{u3}^P$ associated to the component $Ps_{u3}$ of the second-harmonic optical signal $s_{u3}$ has maxima at $\phi_1=\phi_2=0°$ (absolute maxima) and $\phi_1=\phi2=90°$ (relative maxima), i.e., when the first and second optical pump signals $s_{i1}$, $s_{i2}$ have parallel polarizations, and minima at $\phi_1=0°$, $\phi_2=90°$ and at $\phi_1=90°$, $\phi_2=0°$, i.e., when the first and second optical pump signals $s_{i1}$, $s_{i2}$ have polarizations perpendicular to one another.

Experimental maps similar to the ones shown in FIGS. 3a and 4a can be obtained not only for different angles of mutual incidence β but also for different angles of inclination α. In detail, it may be highlighted how, in the case of the component $Ps_{u3}$ (and as regards the case of an optically nonlinear material belonging to the 6 mm crystalline class), variations of the angle of inclination α do not entail variations in the positions of the maxima (absolute and relative maxima), but entail only a reduction of the power associated to the component $Ps_{u3}$ as the angle of inclination α decreases.

Instead, in the case of the component $Ss_{u3}$ (and as regards the case of an optically nonlinear material belonging to the 6 mm crystalline class), different angles of inclination α involve different positions of the maxima. In addition, and once again with reference to the experimental maps S, in the case where the angle of inclination α assumes negative values (i.e., with reference to FIG. 2, it lies to the right of the normal n), a complementary distribution of the absolute maxima and of the relative maxima is found, i.e., it is found that the absolute maxima occur in the case of $\phi_1=0°$, $\phi_2=90°$, and the relative maxima occur in the case of $\phi_1=90°$, $\phi_2=0°$.

Given these premises, the experimental maps can be compared with corresponding numeric maps, i.e., maps that are calculated numerically for the angles of inclination α and of mutual incidence β of the corresponding experimental maps.

In detail, the numeric maps can be obtained on the basis of eqs. (6) and (7), and of normalized coefficients $d_{im}$, which are valid for the crystalline class to which the optically nonlinear material of which the specimen 1 is made belongs.

In the particular case of gallium nitride, to obtain the numeric maps, eqs. (6) and (7) and expressions (13) and (14) are used, assuming a normalized second-order nonlinear optical tensor $\bar{d}$, where the relations $d_{15}=d_{24}=d_{31}=d_{32}=1$ and $d_{33}=-2$ apply, i.e., assuming that the Kleinman symmetry conditions are respected.

Figure 3B:
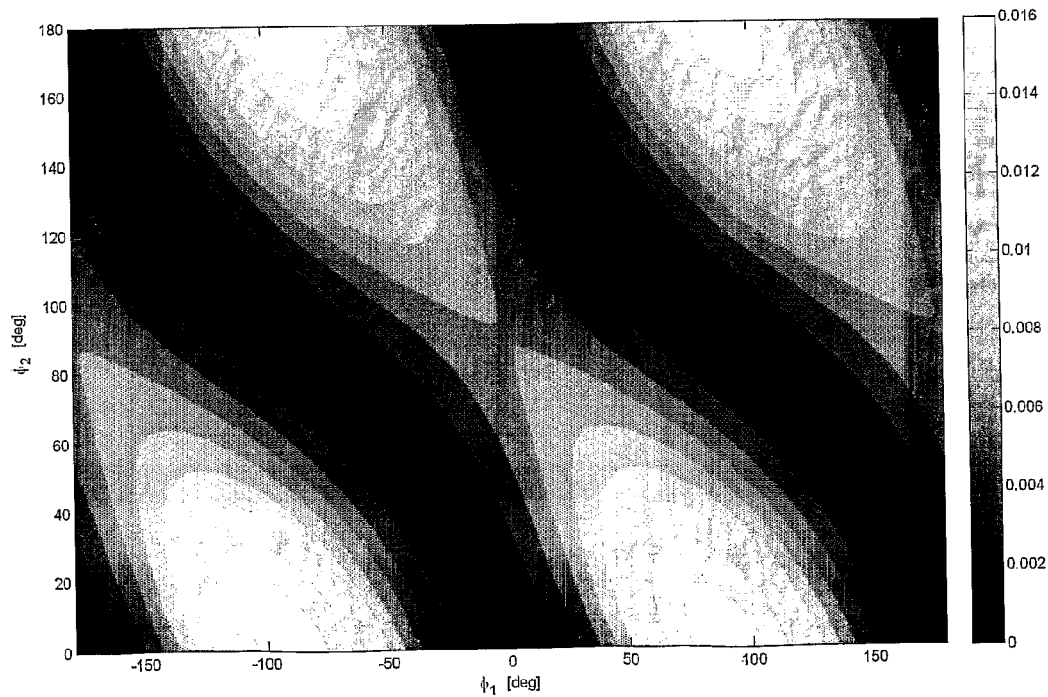
FIGS. 3b and 4b show power maps, respectively of a first component and a second component of a second-harmonic signal, as a function of a first angle and of a second angle, and calculated analytically according to the present invention.
Figure 4B:
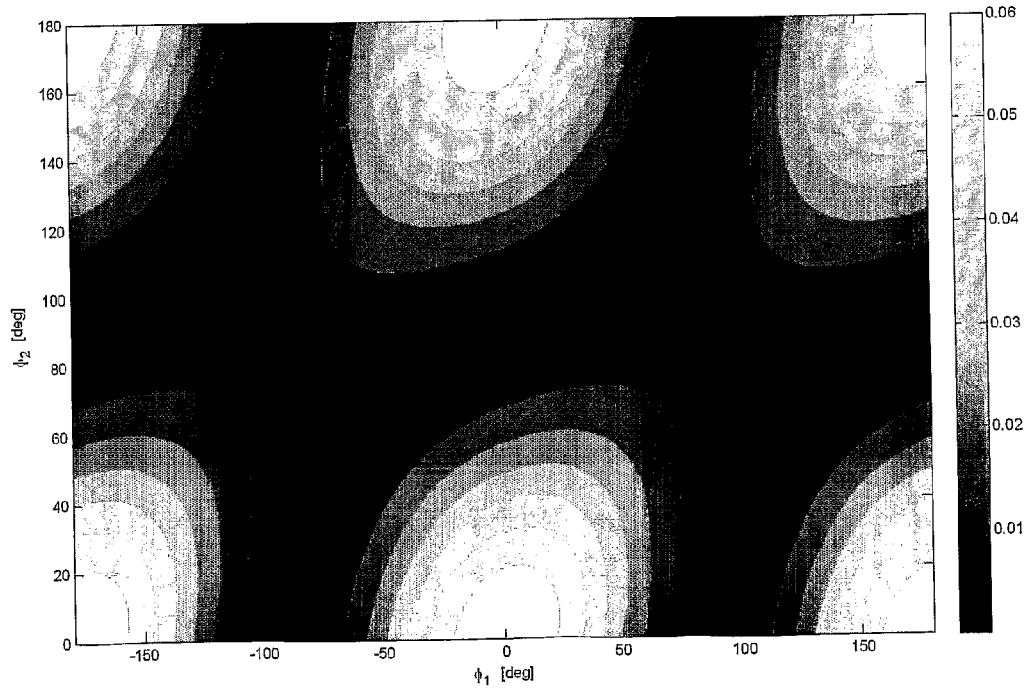

By way of example, FIGS. 3b and 4b show numeric maps corresponding, respectively, to the powers $W_{u3}^S$ and $W_{u3}^P$. In particular, to obtain the numeric maps represented in FIGS. 3b, 4b, an angle of inclination α of 35° and an angle of mutual incidence β of 18° were assumed; in addition, the first polarization angle $\phi_1$ was scanned within an interval comprised between −180° and 180° (with steps of 2°), and the second polarization angle $\phi_2$ within an interval comprised between 0° and 180° (with steps of 2°). The values of the numeric maps represented are normalized values.

From a comparison of at least one experimental map with a corresponding numeric map, it is possible to verify whether the positions of the absolute and relative maxima in the experimental map correspond to the positions of the absolute and relative maxima in the numeric map.

In the case where there is correspondence between the positions of the absolute and relative maxima in the experimental map and in the numeric map, a first ratio and a second ratio are determined, respectively between an absolute maximum and a relative maximum of the experimental map, and an absolute maximum and a relative maximum of the numeric map, the latter two maxima corresponding to the aforementioned absolute maximum and relative maximum of the experimental map. In the case where the first and second ratios are substantially the same as one another, an indication is obtained that for the specimen 1, and hence for the optically nonlinear material, the Kleinman symmetry conditions actually apply. Instead, an indication is obtained that for the specimen 1 the Kleinman symmetry rules do not apply. Said indications have a qualitative nature, given the inevitable tolerances and imprecisions associated to the determination of the experimental maps.

In the case where there is not correspondence between the positions of the absolute and relative maxima of the experimental map and the positions of the absolute and relative maxima of the numeric map, it is possible to assume that the optical axis of the optically nonlinear material of the specimen 1 is not perfectly perpendicular to the surface of incidence 5 of the specimen 1, but that it is rotated about one or more axes x, y, z of the reference system. This misalignment of the optical axis with respect to the normal n to the surface of incidence 5 can be highlighted also by means of crystallographic techniques of a known type, for example, ones which use x-rays, and entails a modification in the expressions of the effective coefficients $d_{\mathit{eff}}^{\phi 1 \phi 2 \to S}(\alpha)$ and $d_{\mathit{eff}}^{\phi 1 \phi 2 \to P}(\alpha)$, which take into account the rotation.

By way of example, in the case where a rotation about the axis z through an angle equal to θ occurs, it is possible to use the following relations:

$$d_{\mathit{eff}}^{\phi 1 \phi 2 \to S}(\alpha) = \cos\theta \cdot [-d_{15}(\sin(\phi_1)\cos(\phi_2)\sin(\alpha_{r2}) + \cos(\phi_1)\sin(\alpha_{r1})\sin(\phi_2))] + -\sin\theta\{-d_{24}\cos(\alpha_{r3})\cos(\phi_1)\cos(\phi_2)[\cos(\alpha_{r1})\sin(\alpha_{r2}) + \sin(\alpha_{r1})\cos(\alpha_{r2})]\} \quad (16)$$

$$d_{\mathit{eff}}^{\phi 1 \phi 2 \to P}(\alpha) = -\cos(\alpha_{r3})\sin\theta \cdot [-d_{15}(\sin(\phi_1)\cos(\phi_2)\sin(\alpha_{r2}) + \cos(\phi_1)\sin(\alpha_{r1})\sin(\phi_2))] + -\cos(\alpha_{r3})\cos\theta\{-d_{24}\cos(\alpha_{r3})\cos(\phi_1)\cos(\phi_2)[\cos(\alpha_{r1})\sin(\alpha_{r1}) + \sin(\alpha_{r1})\cos(\alpha_{r2})]\} + +\sin(\alpha_{r3})d_{31}\sin(\alpha_{r3})\sin(\phi_1)\sin(\phi_2) + \sin(\alpha_{r3})d_{32}\sin(\alpha_{r3})\cos(\phi_1)\cos(\alpha_{r1})\cos(\phi_2)\cos(\alpha_{r2}) + +\sin(\alpha_{r3})d_{33}\sin(\alpha_{r3})\cos(\phi_1)\sin(\alpha_{r1})\cos(\phi_2)\sin(\alpha_{r2}) \quad (17)$$

Then the procedure is like the one described previously.

Similar considerations apply in the case of rotations about another axis (x or y) or else about more than one axis.

It follows that the numeric maps can be used in order to determine possible rotations of the optical axis, and moreover as tool for verifying qualitatively whether the Kleinman conditions are respected.

In the case where the Kleinman symmetry conditions are not satisfied, and it is moreover not legitimate to apply the relations $d_{15}=d_{24}$ and $d_{31}=d_{32}$, for example because it is assumed that the gallium nitride of the specimen 1 has a very irregular crystalline structure, it is possible to determine all the non-zero coefficients $d_{im}$ of the second-order nonlinear optical tensor $\tilde{d}$, i.e., the coefficients $d_{15}, d_{24}, d_{31}, d_{32}, d_{33}$. For this purpose, in addition to the aforementioned experimental maps S and P, the following expressions are used:

$$d_{eff}^{\phi1\phi2\to S}(\alpha) = -d_{15}(\sin(\phi_1)\cos(\phi_2)\sin(\alpha_{r2}) + \cos(\phi_1)\sin(\alpha_{r1})\sin(\phi_2)) \quad (18)$$

$$d_{eff}^{\phi1\phi2\to P}(\alpha) = -d_{24}\cos(\alpha_{r3})\cos(\phi_1)\cos(\phi_2)[\cos(\alpha_{r1}) \sin(\alpha_{r2}) + \sin(\alpha_{r1})\cos(\alpha_{r2})] + -d_{31}\sin(\alpha_{r3})\sin(\phi_1)\sin(\phi_2) - d_{32}\sin(\alpha_{r3})\cos(\phi_1)\cos(\alpha_{r1})\cos(\phi_2)\cos(\alpha_{r2}) + -d_{33}\sin(\alpha_{r3})\cos(\phi_1)\sin(\alpha_{r1})\cos(\phi_2)\sin(\alpha_{r2}) \quad (19)$$

In detail, since the expression (18) is equal to the expression (13), it is possible assume as valid the coefficient $d_{15}$ calculated previously. As regards, instead, the coefficients $d_{24}, d_{31}, d_{32}, d_{33}$, a first subset of measurements of the experimental map P previously obtained is selected, comprising the measurements of power $W_{u3}^P$ which have been obtained with a second polarization angle $\phi_2$ equal to 90°, in such a way that it is legitimate to assume for the effective coefficient $d_{eff}^{\phi1\phi2\to P}(\alpha)$ the following expression:

$$d_{eff}^{\phi1\phi2\to P}(\alpha) = -d_{31}\sin(\alpha_{r3})\sin(\phi_1) \quad (20)$$

Next, on the measurements of the aforementioned first subset of measurements, the least-squares method is applied so as to determine a value of the coefficient $d_{31}$ that minimizes the mean square deviation between the measurements of the first subset and the values yielded by eq. (7) when the coefficient $d_{eff}^{\phi1\phi2\to P}(\alpha)$ has the expression of eq. (20).

Next, a further experimental map P is determined, comprising measurements of the power $W_{u3}^P$, which are obtained in a way similar to what has been described previously, but with a zero angle of inclination $\alpha$, in such a way that also the angle $\alpha_{r3}$ is zero. Since $\alpha_{r3}=0$, it is legitimate to assume for the effective optical coefficient $d_{eff}^{\phi1\phi2\to P}(\alpha)$ the following expression:

$$d_{eff}^{\phi1\phi2\to P}(\alpha) = -d_{24}\cos(\phi_1)\cos(\phi_2)[\cos(\alpha_{r1})\sin(\alpha_{r2}) + \sin(\alpha_{r1})\cos(\alpha_{r2})] \quad (21)$$

It is then possible to apply the least-squares method on the measurements of the further experimental map P in such a way as to determine a value of the coefficient $d_{24}$ that minimizes the mean square deviation between the measurements of the further experimental map P and the values yielded by eq. (7), when the coefficient $d_{eff}^{\phi1\phi2\to P}(\alpha)$ has the expression of eq. (21). It should be noted, however, how, in the case where the operations of preliminary calibration have been carried out with a preliminary angle of inclination $\alpha$ different from zero, it is preferable to determine a new value of the product $W_{i1}*W_{i2}$, to be used in eq. (7). In fact, the operations of preliminary calibration yield a value for the product $W_{i1}*W_{i2}$ that depends upon the preliminary measurement conditions, and in particular upon the preliminary angle of inclination $\alpha$, this being the reason why it is preferable for the first and second measurement conditions to be the same as the preliminary measurement conditions. Consequently, in applying the least-squares method to measurements that are obtained with an angle of inclination $\alpha$ different from the preliminary angle of inclination, it is preferable to use a new value for the product $W_{i1}*W_{i2}$, obtained by means of second operations of preliminary calibration, similar to the operations of preliminary calibration described previously, but with an angle of inclination $\alpha$ equal to zero.

In order to determine the remaining coefficients $d_{32}$ and $d_{33}$, it is possible to consider again the experimental map P calculated previously, and apply the least-squares method on the measurements of the experimental map P in such a way as to determine a pair of values, respectively of the coefficients $d_{32}$ and $d_{33}$, which minimize the mean square deviation between the measurements of the experimental map P and the values yielded by eq. (7), when the effective coefficient $d_{eff}^{\phi1\phi2\to P}(\alpha)$ has the expression of eq. (19), where the values of the coefficients $d_{15}, d_{31}$ and $d_{24}$ previously determined are introduced, thus enabling determination of all the non-zero elements of the second-order nonlinear optical tensor $\tilde{d}$.

According to a further aspect of the present invention, in the case where it is legitimate to assume that the specimen 1 satisfies the Kleinman symmetry conditions, it is possible to follow a procedure for determining the coefficient $d_{15}$ that is different from what has been described, which in what follows will be referred to as alternative determination procedure. Said alternative determination procedure does not envisage determination of the product $W_{i1}*W_{i2}$; hence it does not envisage the operations of preliminary calibration.

In detail, it is possible to adopt the alternative determination procedure in the case where a reference specimen is available made of a reference material, which belongs to the same crystalline class as the optically nonlinear material to be characterized (in the case of gallium nitride, the 6 mm crystalline class), respects the Kleinman symmetry conditions, and the coefficients $d_{im}$ of which are known.

If the aforementioned reference specimen is available, the procedure envisages determining, both for the reference specimen and for the specimen 1, a respective experimental map S, which in what follows will be referred to, respectively, as first experimental map S and second experimental map S. For this purpose, the reference specimen and the specimen 1 are positioned so as to present the same measurement conditions, i.e., the same angle of inclination $\alpha$ and the same angle of mutual incidence $\beta$.

Next, the first experimental map S is considered, corresponding to the reference specimen, and the least-squares method is applied as described previously for the case where it is assumed that the Kleinman symmetry conditions apply, and assuming for the powers $W_{i1}$ and $W_{i2}$ a unit value. In this way, a value indicating the coefficient $d_{15}$ of the reference specimen is determined. By comparing said value indicating the coefficient $d_{15}$ with the known coefficient $d_{15}$, a conversion factor is determined, given by the ratio between the known coefficient $d_{15}$ and the value indicating the coefficient $d_{15}$.

Next, the second experimental map S is considered, corresponding to the specimen 1, and the least-squares method is applied as described previously for the case where it is assumed that the Kleinman symmetry conditions apply. Also in this case, a unit value is assumed for the powers $W_{i1}$ and $W_{i2}$. In this way, a value indicating the coefficient $d_{15}$ of the optically nonlinear material is determined. Next, it is possible to determine the (unknown) coefficient $d_{15}$ of the optically nonlinear material by multiplying the value indicating the coefficient $d_{15}$ of the optically nonlinear material by the conversion factor determined previously.

In a way similar to what has been shown in the case of the example of gallium nitride, it is possible to determine the coefficients $d_{im}$ of optically nonlinear materials having a crystalline structure of a wurtzite type, with non-centrosymmetrical 6 mm point-group symmetry and hexagonal unit cell, such as, for example, cadmium selenide (CdSe), zinc oxide (ZnO), wurtzite zinc sulphide ($\alpha$-ZnS), or else wurtzite silicon carbide ($\alpha$-SiC).

In the case where, instead, the optically nonlinear material has a crystalline structure different from that of gallium nitride, it is in any case possible to proceed to determination of the coefficients $d_{im}$. For example, in the case where the optically nonlinear material has a crystalline structure of the $\underline{4}3$ m type, the second-order nonlinear optical tensor $\tilde{d}$ has the following form:

$$\tilde{d} = \begin{pmatrix} 0 & 0 & 0 & d_{14} & 0 & 0 \\ 0 & 0 & 0 & 0 & d_{25} & 0 \\ 0 & 0 & 0 & 0 & 0 & d_{36} \end{pmatrix} \quad (22)$$

In this case, the effective coefficients $d_{\it{eff}}^{\phi1\phi2 \to S}(\alpha)$ and $d_{\it{eff}}^{\phi1\phi2 \to P}(\alpha)$ assume the following expressions:

$$d_{\it{eff}}^{\phi1\phi2 \to S} = d_{14}\cos(\phi_1)\cos(\phi_2)[\cos(\alpha_{r1})\sin(\alpha_{r3}) + \sin(\alpha_{r1})\cos(\alpha_{r2})] \quad (23)$$

$$d_{\it{eff}}^{\phi1\phi2 \to P} = -\cos(\alpha_{r3})d_{25}\{-\sin(\phi_1)\cos(\phi_2)\sin(\alpha_{r2}) - \sin(\phi_2)\cos(\phi_1)\sin(\alpha_{r1})\} + -\sin(\alpha_{r3})d_{36}\{-\sin(\phi_1)\cos(\phi_2)\cos(\alpha_{r2}) - \sin(\phi_2)\cos(\phi_1)\cos(\alpha_{r1})\} \quad (24)$$

It is, however, possible to reduce further the number of the unknowns to be determined, on the basis of the Kleinman symmetry rules, according to whether the relations $d_{14} = d_{25} = d_{36}$ apply.

In detail, if it is legitimate to assume that the Kleinman symmetry rules apply, it is sufficient to determine, for example, the coefficient $d_{14}$. For this purpose, once the operations of preliminary calibration described previously have been carried out, an experimental map S is determined, aimed at measuring the power $W_{u3}^S$ and obtained in first measurement conditions, preferably identical to the preliminary measurement conditions. Next, the least-squares method is applied to the measurements of the experimental map S so as to determine a value of the coefficient $d_{14}$ that minimizes the mean square deviation between the measurements of the power $W_{u3}^S$ of the experimental map S and the values yielded by eq. (6), when the coefficient $d_{\it{eff}}^{\phi1\phi2 \to S}(\alpha)$ has the expression of eq. (23).

It is in any case possible to determine the coefficients $d_{25}$ and $d_{36}$ in a way independent of the coefficient $d_{14}$. In fact, it is possible to determine an experimental map P, aimed at measuring the power $W_{u3}^P$ and obtained with zero angle of inclination $\alpha$ in such a way that also the angle $\alpha_{r3}$ is zero. Since $\alpha_{r3} = 0$, it is legitimate to assume for the effective nonlinear optical coefficient $d_{\it{eff}}^{\phi1\phi2 \to P}(\alpha)$ the following expression:

$$d_{\it{eff}}^{\phi1\phi2 \to P} = -d_{25}\{-\sin(\phi_1)\cos(\phi_2)\sin(\alpha_{r2}) - \sin(\phi_2)\cos(\phi_1)\sin(\alpha_{r1})\} \quad (25)$$

Next, the least-squares method is applied to the measurements of the experimental map P so as to determine a value of the coefficient $d_{25}$ that minimizes the mean square deviation between the measurements of the power $W_{u3}^P$ of the experimental map P and the values yielded by eq. (7), when the coefficient $d_{\it{eff}}^{\phi1\phi2 \to P}(\alpha)$ has the expression of eq. (25). In a way similar to what has been described as regards the 6 mm crystalline class, also in this case it is preferable, in the case where the operations of preliminary calibration have been carried out with a preliminary angle of inclination $\alpha$ different from zero, to determine a new value of the product $W_{i1}*W_{i2}$, to be used in eq. (7). The new value of the product $W_{i1}*W_{i2}$ can be determined by means of second operations of preliminary calibration, similar to the ones described as regards gallium nitride.

Next, a further experimental map P is determined, aimed at measuring the power $W_{u3}^P$ and obtained preferably in the same first measurement conditions. Then, the least-squares method is applied to the measurements of the further experimental map P so as to determine a value of the coefficient $d_{36}$ that minimizes the mean square deviation between the measurements of the power $W_{u3}^P$ of the further experimental map P and the values yielded by eq. (7), when the effective coefficient $d_{\it{eff}}^{\phi1\phi2 \to P}(\alpha)$ has the expression of eq. (24), where the value of the coefficient $d_{25}$ determined previously is used. In this way, the coefficients $d_{14}$, $d_{25}$, $d_{36}$ are determined independently, with consequent possibility of verifying a posteriori that the Kleinman symmetry conditions are respected.

It may likewise be noted that, in a way similar to what has been described as regards the 6 mm crystalline class, also for the optically nonlinear materials belonging to the $\underline{4}3$ m crystalline class it is possible to use an alternative determination procedure, provided that it is legitimate to assume that the specimen 1 respects the Kleinman symmetry conditions and an appropriate reference specimen is available. In detail, the reference specimen must respect the Kleinman symmetry conditions and must being made of a reference material belonging to the $\underline{4}3$ m crystalline class, it being necessary for the coefficients $d_{im}$ of said reference material to be known.

In the case of the $\underline{4}3$ m crystalline class, the alternative determination procedure is similar to the one described as regards the 6 mm crystalline class. In greater detail, it is assumed that the powers $W_{i1}$ and $W_{i2}$ have a unit value, and, on a first experimental map S and a second experimental map S, corresponding, respectively, to the reference specimen and to the specimen 1, the operations described previously are carried out. In this way, a conversion factor, a value indicating the coefficient $d_{14}$, and, finally, the coefficient $d_{14}$ itself are determined.

Once again by way of example, in the case where the optically nonlinear material has a crystalline structure of the $\underline{3}$m type, the second-order nonlinear optical tensor $\tilde{d}$ has the following form:

$$\tilde{d} = \begin{pmatrix} 0 & 0 & 0 & 0 & d_{15} & -d_{22} \\ -d_{22} & d_{22} & 0 & d_{15} & 0 & 0 \\ d_{31} & d_{31} & d_{33} & 0 & 0 & 0 \end{pmatrix} \quad (26)$$

Consequently, the effective coefficients $d_{\it{eff}}^{\phi1\phi2 \to S}(\alpha)$ and $d_{\it{eff}}^{\phi1\phi2 \to P}(\alpha)$ assume the following expressions:

$$d_{\it{eff}}^{\phi1\phi2 \to S} = d_{15}\{-\sin(\phi_1)\cos(\phi_2)\sin(\alpha_{r2}) - \sin(\phi_2)\cos(\phi_1)\sin(\alpha_{r1})\} + -d_{22}\{-\sin(\phi_1)\cos(\phi_2)\cos(\alpha_{r2}) - \sin(\phi_2)\cos(\phi_1)\cos(\alpha_{r1})\} \quad (27)$$

$$d_{\it{eff}}^{\phi1\phi2 \to P} = -\cos(\alpha_{r3})d_{22}[\cos(\phi_1)\cos(\alpha_{r1})\cos(\phi_2)\cos(\alpha_{r2}) - \sin(\phi_1)\sin(\phi_2)] + -\cos(\alpha_{r3})d_{15}\cos(\phi_1)\cos(\phi_2)[\cos(\alpha_{r1})\sin(\alpha_{r2}) + \sin(\alpha_{r1})\cos(\alpha_{r2})] + -\sin(\alpha_{r3})\{d_{31}[\cos(\phi_1)\cos(\alpha_{r1})\cos(\phi_2)\cos(\alpha_{r2}) + \sin(\phi_1)\sin(\phi_2)] + d_{33}\cos(\phi_1)\sin(\alpha_{r1})\cos(\phi_2)\sin(\alpha_{r2})\} \quad (28)$$

There are hence four unknowns to be determined ($d_{15}$, $d_{22}$, $d_{31}$, $d_{33}$), which reduce to three ($d_{15}$, $d_{22}$, $d_{33}$) in the case where the Kleinman symmetry conditions apply, which entail the relation $d_{31} = d_{15}$. In what follows the more general case is described, where the Kleinman symmetry rules are not resorted to.

In detail, after prior execution of the operations of preliminary calibration described previously, an experimental map P and an experimental map S are determined, preferably in the same preliminary measurement conditions.

Next, a first subset of measurements is selected, comprising the measurements of power $W_{u3\ 3}^S$ of the experimental map S which have been obtained with the first polarization angle $\phi_1$ equal to 90°, in such a way that it is legitimate to assume for the effective coefficient $d_{e\!f\!f}^{\phi 1 \phi 2 \to S}(\alpha)$ the following expression:

$$d_{e\!f\!f}^{\phi 1 \phi 2 \to S} = d_{15}\{-\cos(\phi_2)\sin(\alpha_{r2})\} - d_{22}\{-\cos(\phi_2)\cos(\alpha_{r2})\} \quad (29)$$

A second subset of measurements is moreover selected, comprising the measurements of power $W_{u3}^S$ of the experimental map S which have been obtained with the first polarization angle $\phi_1$ equal to 0°, in such a way that it is legitimate to assume for the effective coefficient $d_{e\!f\!f}^{\phi 1 \phi 2 \to S}(\alpha)$ the following expression:

$$d_{e\!f\!f}^{\phi 1 \phi 2 \to S} = d_{15}\{-\sin(\phi_2)\sin(\alpha_{r1})\} - d_{22}\{-\sin(\phi_2)\cos(\alpha_{r1})\} \quad (30)$$

By applying the least-squares method to the measurements of the first and second subsets, it is possible to determine the values of the coefficients $d_{15}$ and $d_{22}$ that minimize the mean square deviation between the measurements of the first subset and the values yielded by eq. (6) when expression (29) applies, and between the measurements of the second subset and the values yielded by eq. (6) when expression (30) applies. In this connection, it should be noted that, in general, given an experimental map formed by N×M values, i.e., given an experimental map obtained assigning N different values to the first polarization angle $\phi_1$ and M different values to the second polarization angle $\phi_2$, it is again possible to obtain a system of N+M equations, of which at least L=min(N,M) are independent. Consequently, it is once again possible to obtain a number of unknowns equal to L.

Next, the experimental map P is considered, and a third subset of measurements is selected, comprising the measurements of power $W_{u3}^P$ which have been obtained with the first polarization angle $\phi_1$ equal to 90°, in such a way that it is legitimate to assume for the effective coefficient $d_{e\!f\!f}^{\phi 1 \phi 2 \to P}(\alpha)$ the following expression:

$$d_{e\!f\!f}^{\phi 1 \phi 2 \to P} = -\cos(\alpha_{r3})d_{22}[-\sin(\phi_2)] - \sin(\alpha_{r3})\{d_{31}[\sin(\phi_2)]\} \quad (31)$$

Next, the least-squares method is applied so as to determine a value of the coefficient $d_{31}$ that minimizes the mean square deviation between the measurements of the power $W_{u3}^P$ of the third subset and the values yielded by eq. (7), when the coefficient $d_{e\!f\!f}^{\phi 1 \phi 2 \to P}(\alpha)$ has the expression of eq. (31), where the value of the coefficient $d_{22}$ previously determined is used.

Next, the entire experimental map P is considered, and the least-squares method is applied so as to determine a value of the coefficient $d_{33}$ that minimizes the mean square deviation between the measurements of the power $W_{u3}^P$ of the experimental map P and the values yielded by eq. (7), when the coefficient $d_{e\!f\!f}^{\phi 1 \phi 2 \to P}(\alpha)$ has the expression of eq. (28), where the values of the coefficients $d_{15}$, $d_{22}$, $d_{31}$ previously determined are used.

It should be noted how, in the case where it is legitimate to assume a priori that the specimen 1 respects the Kleinman symmetry conditions, it is not necessary to determine the coefficient $d_{31}$, in so far as the relation $d_{31}=d_{15}$ applies. In addition, in this case, and in a way similar to what is described as regards the 6 mm and $\underline{4}3$ m crystalline classes, it is possible to adopt an alternative determination procedure, provided that an appropriate reference specimen is available, which respects the Kleinman symmetry conditions, is made of a reference material belonging to the $\underline{4}3$ m crystalline class, and has known coefficients $d_{im}$.

In the case of the $\underline{3}$m crystalline class, the alternative determination procedure envisages determining a first experimental map S and a first experimental map P, both corresponding to the reference specimen, and moreover a second experimental map S and a second experimental map P, both corresponding to the specimen 1. Next, on the experimental maps corresponding to the reference specimen and the experimental maps corresponding to the specimen 1, the operations described previously regarding the case where it is assumed that the Kleinman symmetry conditions are respected are iterated, assuming that the powers $W_{i1}$ and $W_{i2}$ have a unit value. On the basis of the experimental maps corresponding to the reference specimen, first values are determined, indicating the coefficients $d_{15}$, $d_{22}$, $d_{33}$ of the reference specimen, whilst, on the basis of the experimental maps corresponding to the specimen 1, second values are determined, indicating the coefficients $d_{15}$, $d_{22}$, $d_{33}$ of the specimen 1. Since, but for the inevitable imprecisions of measurement and the numeric tolerances, the first values are all substantially in one and the same ratio with the corresponding (known) coefficients $d_{15}$, $d_{22}$, $d_{33}$ of the reference specimen, said ratio can be assumed as conversion factor. On the basis of said conversion ratio and of the second values, it is hence possible to determine the coefficients $d_{15}$, $d_{22}$, $d_{33}$ of the specimen 1.

Once again by way of example, in the case where the optically nonlinear material has, instead, a crystalline structure of the 32 type, the second-order nonlinear optical tensor $\tilde{d}$ has the following form:

$$\tilde{d} = \begin{pmatrix} d_{11} & -d_{11} & 0 & d_{14} & 0 & 0 \\ 0 & 0 & 0 & 0 & -d_{14} & -d_{11} \\ 0 & 0 & 0 & 0 & 0 & 0 \end{pmatrix} \quad (32)$$

It should be noted that the second-order nonlinear optical tensor $\tilde{d}$ given in eq. (32) does not undergo any modifications due to the Kleinman symmetry rules.

The effective coefficients $d_{e\!f\!f}^{\phi 1 \phi 2 \to S}(\alpha)$ and $d_{e\!f\!f}^{\phi 1 \phi 2 \to P}(\alpha)$ assume the following expressions:

$$d_{e\!f\!f}^{\phi 1 \phi 2 \to S} = d_{11}[\sin(\phi_1)\sin(\phi_2)-\cos(\phi_1)\cos(\alpha_{r1})\cos(\phi_2)\cos(\alpha_{r2})] + d_{14}\cos(\phi_1)\cos(\phi_2)[\cos(\alpha_{r1})\sin(\alpha_{r2}) + \sin(\alpha_{r1})\cos(\alpha_{r2})] \quad (33)$$

$$d_{e\!f\!f}^{\phi 1 \phi 2 \to P} = \cos(\alpha_{r3})d_{14}[-\sin(\phi_1)\cos(\phi_2)\sin(\alpha_{r2})-\sin(\phi_2)\cos(\phi_1)\sin(\alpha_{r1})] + \cos(\alpha_{r3})d_{11}[-\sin(\phi_1)\cos(\phi_2)\cos(\alpha_{r2})-\sin(\phi_2)\cos(\phi_1)\cos(\alpha_{r1})] \quad (34)$$

Operatively, in order to determine the unknown coefficients $d_{11}$ and $d_{14}$, it is possible to determine an experimental map S and an experimental map P, which are preferably obtained in the same preliminary measurement conditions.

Next, the experimental map S is considered, and a first subset of measurements is selected, comprising the measurements of power $W_{u3}^S$ which have been obtained with the first polarization angle $\phi_1$ equal to 90°, in such a way that it is legitimate to assume for the effective optical coefficient $d_{e\!f\!f}^{\phi 1 \phi 2 \to S}(\alpha)$ the following expression:

$$\tilde{d}_{e\!f\!f}^{\phi 1 \phi 2 \to S} = d_{11}[\sin(\phi_2)] \quad (35)$$

Then the least-squares method is applied to the measurements of the first subset so as to determine a value of the coefficient $d_{11}$ that minimizes the mean square deviation between the measurements of the power $W_{u3}^S$ of the first subset and the values yielded by eq. (6) when the coefficient $d_{e\!f\!f}^{\phi 1 \phi 2 \to S}(\alpha)$ has the expression of eq. (35).

Next, the entire experimental map P is considered, and the least-squares method is applied so as to determine a value of the coefficient $d_{14}$ that minimizes the mean square deviation between the measurements of the power $W_{u3}^P$ of the experimental map P and the values yielded by eq. (7) when the coefficient $d_{\mathit{eff}}^{\phi_1\phi_2\to P}(\alpha)$ has the expression of eq. (34), where the value of the coefficient $d_{11}$ determined previously is used.

Also in the case of the 32 crystalline class it is possible to adopt an alternative determination procedure, provided that a reference specimen is available made of a reference material belonging to the 32 crystalline class and the coefficients $d_{im}$ of which are known.

The alternative determination procedure envisages determining a first experimental map S and a first experimental map P, corresponding to the reference specimen, and moreover a second experimental map S and a second experimental map P, corresponding to the specimen 1. Next, on the experimental maps corresponding to the reference specimen and on the experimental maps corresponding to the specimen 1, the operations described previously are iterated, assuming that the powers $W_{i1}$ and $W_{i2}$ have a unit value. On the basis of the experimental maps corresponding to the reference specimen, first values are determined, indicating the coefficients $d_{11}$, $d_{14}$ of the reference specimen, whilst, on the basis of the experimental maps corresponding to the specimen 1, second values are determined, indicating the coefficients $d_{11}$, $d_{14}$ of the specimen 1. Since, but for the inevitable measurement imprecisions and the numeric tolerances, the first values are substantially in one and the same ratio with the corresponding (known) coefficients $d_{11}$, $d_{14}$ of the reference specimen, said ratio can be assumed as conversion factor. On the basis of said conversion ratio, it is hence possible to determine the coefficients $d_{11}$, $d_{14}$ of the specimen 1.

The present method can be implemented by means of the system 20 for determining the coefficients $d_{im}$ shown in FIG. 5. In detail, the determination system 20 comprises:
- an optical source 21, designed to generate quasi-monochromatic electromagnetic radiation at a pulsation $\omega_i$;
- an optical beam splitter 22, having a shape and arrangement with respect to the optical source 21 such that it is designed to receive at input the quasi-monochromatic electromagnetic radiation and to consequently generate at output the first and second optical pump signals $s_{i1}$, $s_{i2}$, and to route them respectively towards the first and second optical paths 10a, 10b;
- a first reflecting surface 23a and a second reflecting surface 23b, which are set along the first optical path 10a and the second optical path 10b, respectively, so as to receive the optical pump signals $s_{i1}$, $s_{i2}$ generated by the optical beam splitter 22;
- a first polarizer plate 24a and a second polarizer plate 24b, for example of the half-wave type, which are set along the first optical path 10a and the second optical path 10b, respectively, downstream of the reflecting surfaces 23a, 23b and so as to receive the optical pump signals $s_{i1}$, $s_{i2}$ reflected by the reflecting surfaces 23a, 23b;
- a first focussing lens 25a and a second focussing lens 25b, which are set along the first optical path 10a and the second optical path 10b, respectively, downstream of the polarizer plates 24a, 24b and so as to receive the optical pump signals $s_{i1}$, $s_{i2}$ at output from the polarizer plates 24a, 24b;
- a support 26, designed to carry a generic specimen (here designated by 35) made at least in part of an optically nonlinear material, the coefficients $d_{im}$ of which are to be determined; the support 26 is such that the specimen 35 receives the optical pump signals $s_{i1}$, $s_{i2}$ focussed by the focussing lenses 25a, 25b so as to generate the second-harmonic optical signal $s_{u3}$ with pulsation equal to $2\omega_i$, as described previously;
- actuator means (not illustrated), designed to vary the position of the specimen 35, and in particular to vary the angle of inclination $\alpha$;
- a polarization-selector device 27, for example a Polaroid filter, capable of filtering selectively and in a controllable way the component $Ps_{u3}$ or the component $Ss_{u3}$ of the second-harmonic optical signal $s_{u3}$ at output from the specimen 35;
- a focussing device 28 (optional) and an optical fibre 29, for example of a single-mode type, which are arranged with respect to the polarization-selector device 27 in such a way that the focussing device 28 will focus the component ($Ps_{u3}$ or $Ss_{u3}$) of the second-harmonic optical signal $s_{u3}$ selected by the polarization-selector device 27 in the optical fibre 29;
- a photon-counter device 30, which is coupled to the optical fibre 29 and is designed to supply measurements of the power associated to the component ($Ps_{u3}$ or $Ss_{u3}$) of the second-harmonic optical signal $s_{u3}$ selected by the polarization-selector device 27; and
- a processing unit 31, connected to the photon-counter device 30 and designed to implement the operations described previously, and in particular to apply the least-squares method as described previously so as to determine the effective second-order nonlinear optical coefficients $d_{im}$.

In greater detail, and by way of example, the optical source 21 can comprise a titanium-sapphire laser of the mode-locked type, tuned at a wavelength $\lambda$ of 830 nm and actuated so as to generate pulses with amplitude equal to 130 fs and repetition rate of said pulses equal to 76 MHz. The electromagnetic radiation thus generated is then divided by the optical beam splitter 22 in such a way that the aforementioned first and second optical pump signals $s_{i1}$, $s_{i2}$ will have substantially the same intensity.

The half-wave polarizer plates 24a, 24b can be controlled, in a way in itself known, in such a way that the first and second optical signals $s_{i1}$, $s_{i2}$ impinge upon the specimen 35 with pre-set polarizations. By means of the half-wave polarizer plates 24a, 24b it is hence possible to control the first and second polarization angles $\phi_1$, $\phi_2$. Said half-wave polarizer plates 24a, 24b are formed in such a way as to not introduce nonlinearities.

The optical source 21, the optical beam splitter 22, the reflecting surfaces 23a, 23b, the half-wave polarizer plates 24a, 24b, the focussing lenses 25a, 25b and the support 26 are arranged in such a way that the optical pump signals $s_{i1}$, $s_{i2}$ impinge upon the specimen 35 in compliance with what has been described as regards FIG. 2.

In order to enable compensation for possible differences in length of the first optical path 10a and of the second optical path 10b, it is possible to use at least one delay line of a known type, inserted in one of the optical paths 10a, 10b themselves, or else in the point of generation of the first and second optical pump signals $s_{i1}$, $s_{i2}$ (the optical beam splitter 22) in such a way that the optical pump signals $s_{i1}$, $s_{i2}$ will impinge upon the specimen at the same instants of time. For example, it is possible to use a device (not shown) for translation of the optical beam splitter 22, designed to translate the optical beam splitter 22 itself in such a way that the optical beam splitter 22 will function as delay line.

Operatively, it is possible to obtain an experimental map by acting on the polarizer plates 24a, 24b so as to vary the angles of polarization $\phi_1$ and $\phi_2$, selecting with the polarization-selector device 27 the component $Ps_{u3}$ or $Ss_{u3}$ of the second-harmonic optical signal $s_{u3}$ to which the experimental map refers, and measuring the power ($W_{u3}^P$ and $W_{u3}^S$) of said component by means of the photon-counter device 30. Processing of the experimental maps is then entrusted to the processing unit 31.

The present method hence enables determination of the coefficients $d_{lm}$ of an optically nonlinear material without any need to perform rotations of the specimen, with consequent lower complexity of implementation of the method itself, in addition to a lower dependence upon possible irregularities present in the specimen. For this purpose, the present method envisages, given an optically nonlinear material belonging to a crystalline class, determining a number of sets of measurements (the experimental maps and/or the subsets of the experimental maps) and applying the least-squares method to each set of measurements on the basis of a respective parametric function (see eqs. 6, 7 and the expressions of the effective coefficients $d_{\textit{eff}}^{\phi 1 \phi 2 \to S}(\alpha)$ and $d_{\textit{eff}}^{\phi 1 \phi 2 \to P}(\alpha)$). The number of measurement sets, and possibly also the measurement conditions (in the case in point, the angle of inclination $\alpha$), depend upon the crystalline class, and in particular upon the form of the second-order nonlinear optical tensor ($\bar{d}$) associated to said crystalline class. According to the crystalline class, it is moreover possible for one or more of said measurement sets to comprise measurements which are obtained by fixing one of the two angles of polarization $\phi_1$ and $\phi_2$ to a pre-set value and varying the other.

Finally, it is evident that modifications and variations may be made to the present method for determining the second-order nonlinear optical coefficients and to the present determination system, without thereby departing from the scope of the present invention, as defined by the annexed claims.

For example, as regards the operations of preliminary calibration, they can be performed in a way different from the one described. For instance, the preliminary measurements may be obtained by varying both the first polarization angle $\phi_1$ and the second polarization angle $\phi_2$.

In addition, according to the crystalline class to which the optically nonlinear material present in the specimen belongs, it is possible for there to be a number of ways of determining the non-zero elements of the second-order nonlinear optical tensor $\bar{d}$. In this connection, the examples described as regards the 6 mm, $\underline{4}3$ m, $\underline{3}$m and 32 crystallographic classes are to be considered as non-exhaustive, given that in general it is possible to consider also other crystalline classes.

Again, instead of the least-squares method, it is possible to use other known fitting techniques, such as, for example, the singular-value-decomposition method, the Monte Carlo method, the Tikhonov regularization method, etc.

As regards the specimen, it is possible to use specimens with shapes different from the one illustrated. For example, the substrate 2 may be absent. In addition the specimen may have a non-parallelepipedal shape.

As regards the generation of the optical pump signals $s_{i1}$, $s_{i2}$, they can have pulsations that differ from one another, for example, equal to $\omega_1$ and $\omega_2$, the second-harmonic optical signal $s_{u3}$ hence having a pulsation equal to $\omega_1+\omega_2$. In this case, the generation of a signal $s_{u3}$ having a sum frequency is referred to as sum-frequency generation (SFG), and eqs. (6) and (7) can be generalized, respectively, as follows:

$$W_{u3}^S(\alpha) = \left(\frac{512\pi^3}{A_1 \cdot A_2}\right) \cdot (t_{i1}^{\phi 1})^2 \cdot (t_{i2}^{\phi 2})^2 \cdot T_{\omega_1+\omega_2}^S \cdot \quad (36)$$

$$W_{i1} \cdot W_{i2} \frac{\sin^2(\Psi_{SFG}^{\phi 1 \phi 2 \to S}(\alpha))}{\left[n_{i1}^{\phi 1}(\omega_1) \cdot n_{i2}^{\phi 2}(\omega_2) - n_{u3}^S(\omega_1+\omega_2)^2\right]^2} (d_{\textit{eff}}^{\phi 1 \phi 2 \to S}(\alpha))^2$$

$$W_{u3}^P(\alpha) = \left(\frac{512\pi^3}{A_1 \cdot A_2}\right) \cdot (t_{i1}^{\phi 1})^2 \cdot (t_{i2}^{\phi 2})^2 \cdot T_{\omega_1+\omega_2}^P \cdot W_{i1} \cdot \quad (37)$$

$$W_{i2} \frac{\sin^2(\Psi_{SFG}^{\phi 1 \phi 2 \to P}(\alpha))}{\left[n_{i1}^{\phi 1}(\omega_1) \cdot n_{i2}^{\phi 2}(\omega_2) - n_{u3}^P(\omega_1+\omega_2)^2\right]^2} (d_{\textit{eff}}^{\phi 1 \phi 2 \to P}(\alpha))^2$$

As compared to eqs. (6) and (7):
- $T_{\omega_1+\omega_2}^S$ and $T_{\omega_1+\omega_2}^P$ are the Fresnel transmission coefficients for the sum-frequency optical signal $s_{u3}$ at output from the specimen, hence with pulsation $\omega_1+\omega_2$, in the case of sum-frequency optical signal $s_{u3}$ with S polarization and P polarization, respectively;
- $n_{i1}^{\Phi 1}(\omega_1)$ and $n_{i2}^{\Phi 2}(\omega_2)$ are the refractive indices of the optically nonlinear material, respectively for the first optical pump signal $s_{i1}$ and the second optical pump signal $s_{i2}$, hence at the pulsations $\omega_1$ and $\omega_2$;
- $n_{u3}^S(\omega_1+\omega_2)$ and $n_{u3}^P(\omega_1+\omega_2)$ are the refractive indices of the optically nonlinear material at the pulsation $\omega_1+\omega_2$, respectively for the component $Ss_{u3}$ and the component $Ps_{u3}$ of the sum-frequency optical signal $s_{u3}$;
- $\Psi_{SFG}^{\Phi 1 \Phi 2 \to S}(\alpha)$ and $\Psi_{SFG}^{\Phi 1 \Phi 2 \to P}(\alpha)$ are the phase factors corresponding, respectively, to the component $Ss_{u3}$ and to the component $Ps_{u3}$, and have the following expressions:

$$\Psi_{SFG}^{\phi 1 \phi 2 \to S}(\alpha) = \left(\frac{\pi L}{2}\right)\left(\frac{2}{\lambda}\right)[n_{i1}^{\phi 1}(\omega_1) \cdot \cos(\alpha_{r1}) + \quad (38)$$
$$n_{i2}^{\phi 2}(\omega_2) \cdot \cos(\alpha_{r2}) - 2n_{u3}^S(\omega_1+\omega_2) \cdot \cos(\alpha_{r3})]$$

$$\Psi_{SFG}^{\phi 1 \phi 2 \to P}(\alpha) = \left(\frac{\pi L}{2}\right)\left(\frac{2}{\lambda}\right)[n_{i1}^{\phi 1}(\omega_1) \cdot \cos(\alpha_{r1}) + \quad (39)$$
$$n_{i2}^{\phi 2}(\omega_2) \cdot \cos(\alpha_{r2}) - 2n_{u3}^P(\omega_1+\omega_2) \cdot \cos(\alpha_{r3})]$$

As regards the determination system 20, also this may be different from the one illustrated in FIG. 5. For example, it is possible to use a light source 21 of a type different from what has been described, such as, for example, an optical source of a non-pulsed type connected to a parametric optical oscillator (not shown), in order to obtain two quasi-monochromatic optical signals with different pulsations, for example, equal to $\omega_1$ and $\omega_2$, the frequency of which can be adjusted with continuity over a certain interval, provided that the sum of the pulsations $\omega_1$ and $\omega_2$ is equal to the pulsation of the optical source.

The invention claimed is:

1. A method for determining second-order nonlinear optical coefficients of a non-centrosymmetrical material, comprising:
   providing a specimen made at least in part of said material,
   causing a first optical signal and a second optical signal having a first pulsation and a second pulsation and a first polarization state and a second polarization state, respectively, to impinge upon said specimen in such a way that said specimen generates a sum optical signal having a third pulsation and a third polarization state, said third pulsation being equal to the sum of said first and second pulsations, said third polarization state being a function of said first and second polarization states, wherein causing the first optical signal and the second optical signal to impinge upon said specimen includes causing impingement of said first and second optical signals with linear polarizations in such a way that said sum optical signal is linearly polarized, said first and second polarization states being defined, respectively, by a first polarization angle and a second polarization angle;

determining a plurality of measurements of power associated to said sum optical signal, and determining said second-order nonlinear optical coefficients on the basis of said plurality of measurements of power;

wherein the step of determining the plurality of measurements of power includes performing measurements of power of said sum optical signal as said first and second polarization states vary, and includes the step of varying said first and second polarization angles by means of polarizing means controllable to vary said first and second polarization angles in such a way that they assume a plurality of pairs of respective values, said values being comprised in a range with a width of at least 180°.

2. The method according to claim 1, wherein said polarizing means are controllable to vary said first and second polarization angles in the ranges between [−180°;180°] and [0°; 180°], respectively.

3. The method according to claim 2, wherein causing a first optical signal and a second optical signal to impinge upon said specimen comprises generating said first and second optical signals in such a way that they have directions of propagation lying in one and the same plane and form between them an angle of mutual incidence, a bisectrix of said angle of mutual incidence forming an angle of inclination with respect to a normal to said specimen, said first and second optical signals forming with said normal, respectively, a first angle of incidence and a second angle of incidence, said sum optical signal having a direction of propagation lying in said plane and comprising a first orthogonal component and a second orthogonal component, which have directions of polarization that are, respectively, perpendicular and parallel to said plane, each of said first and second polarization angles being equal to 0° and 90° respectively when the corresponding optical signal is polarized parallel or orthogonally to said plane.

4. The method according to claim 3, wherein performing measurements of power of said sum optical signal as said first and second polarization states vary comprises obtaining a number of sets of measurements, each set of measurements being obtained by:

setting for said angle of mutual incidence and said angle of inclination values of configuration associated to said each set of measurements;

selecting a respective orthogonal component, chosen between said first orthogonal component and said second orthogonal component;

varying said first and second polarization angles in such a way that they assume a respective number of pairs of respective values; and for each pair of said respective number of pairs, determining a measurement of power associated to said respective orthogonal component.

5. The method according to claim 4, wherein determining said second-order nonlinear optical coefficients on the basis of said plurality of measurements of power comprises:

establishing said number of sets of measurements and the corresponding values of configuration as a function of an arrangement of non-zero second-order nonlinear optical coefficients in a second-order nonlinear optical tensor of said material; and applying numeric fitting to each set of measurements of said number of sets of measurements, on the basis of a respective parametric function, said parametric function comprising one or more of said second-order nonlinear optical coefficients as respective parameters, the application of said numeric fitting yielding values of said respective parameters that minimize a deviation between the measurements of said each set of measurements and corresponding values given by said respective parametric function.

6. The method according to claim 5, wherein performing measurements of power further comprises determining a number of additional sets of measurements, said additional sets of measurements being related to a reference specimen of which the values of the second-order nonlinear optical coefficients are known, said reference specimen belonging to the same crystalline class to which said material belongs, each additional set of measurements being associated to a corresponding set of measurements of said number of sets of measurements, each additional set of measurements and each corresponding set of measurements referring to one and the same orthogonal component and having the same configuration values; said method further comprising the step of applying the method of numeric fitting to each additional set of measurements on the basis of the same respective parametric function used applying the method of numeric fitting to the corresponding set of measurements.

7. The method according to claim 6, wherein applying the method of numeric fitting to each additional set of measurements yields at least one quantity indicating a nonlinear optical coefficient of said reference specimen, said method further comprising determining a conversion factor on the basis of said at least one quantity indicating a nonlinear optical coefficient and of at least one corresponding value of said known values of the second-order nonlinear optical coefficients of said reference specimen.

8. The method according to claim 7, wherein applying the method of numeric fitting to each set of measurements of said number of sets of measurements yields at least one quantity indicating a nonlinear optical coefficient of said material, said method further comprising determining said second-order nonlinear optical coefficients of said material on the basis of said at least one quantity indicating a nonlinear optical coefficient of said material and of said conversion factor.

9. The method according to claim 5, wherein said respective parametric function further comprises a power parameter equal to the product of the powers with which said first and second optical signals impinge upon said specimen, said method further comprising determining said power parameter on the basis of a set of reference measurements corresponding to a reference specimen, of which the values of the second-order nonlinear optical coefficients are known.

10. The method according to claim 9, wherein providing a specimen comprises providing a specimen made at least in part of a material having crystalline structure belonging to the 6mm crystalline class, wherein said number of sets of measurements comprises a first set, which is associated to said first orthogonal component, and wherein applying the numeric fitting comprises applying the numeric fitting to said first set and on the basis of a first parametric function, having the following expression:

$$W_{u3}^{S}(\alpha) = K^{S} \cdot (d_{\mathit{eff}}^{\phi 1 \phi 2 \to S}(\alpha))^2$$

where $K^S$ is a first proportionality function, and where:

$$d_{\mathit{eff}}^{\phi 1 \phi 2 \to S}(\alpha) = -d_{15}(\sin(\phi_1)\cos(\phi_2)\sin(\alpha_{r\text{-}2}) + \cos(\phi_1)\sin(\alpha_{r\text{-}1})\sin(\phi_2))$$

where $\phi_1$ and $\phi_2$ are said first and second polarization angles, $d_{15}$ is a second-order nonlinear optical coefficient, and $\alpha_{r1}$ and $\alpha_{r2}$ are angles of refraction corresponding, respectively, to said first and second optical signals.

11. The method according to claim 10, wherein said number of sets of measurements further comprises:
   a second set, which is associated to said second orthogonal component and in which said respective number of pairs of respective values comprises pairs of values such that said first polarization angle ($\phi_1$) is equal to 90°; and
   a third set, which is associated to said second orthogonal component;
and wherein applying the numeric fitting comprises applying the numeric fitting to said second and third sets, respectively on the basis of a second parametric function and a third parametric function, which have, respectively, the following expressions:

$$W_{u3}^P(\alpha) = K^P \cdot (d_{\mathit{eff}\_1}^{\phi1\phi2 \to P}(\alpha))^2$$

$$W_{u3}^P(\alpha) = K^P \cdot (d_{\mathit{eff}\_2}^{\phi1\phi2 \to P}(\alpha))^2$$

where $K^P$ is a second proportionality function, and where:

$$d_{\mathit{eff}\_1}^{\phi1\phi2 \to P}(\alpha) = -d_{31}\sin(\alpha_{r3})\sin(\alpha_2)$$

$$d_{\mathit{eff}\_2}^{\phi1\phi2 \to P}(\alpha) = -d_{15}\cos(\alpha_{r3})\cos(\phi_1)\cos(\phi_2)[\cos(\alpha_{r1})\sin(\alpha_{r2}) + \sin(\alpha_{r1})\cos(\alpha_{r2})] + -d_{31}[\sin(\alpha_{r3})\sin(\phi_1)\sin(\phi_2) + \sin(\alpha_{r3})\cos(\phi_1)\cos(\alpha_{r1})\cos(\phi_2)\cos(\alpha_{r2})] + -d_{33}\sin(\alpha_{r3})\cos(\phi_1)\sin(\alpha_{r1})\cos(\phi_2)\sin(\alpha_{r2})$$

where $d_{31}$ and $d_{33}$ are second-order nonlinear optical coefficients, and $\alpha_{r3}$ is an angle of refraction corresponding to said sum optical signal.

12. The method according claim 10, wherein said first and second proportionality functions $K^S$ and $K^P$ have the following expressions:

$$K^S = \left(\frac{512\pi^3}{A_1 * A_2}\right) \cdot (t_{i1}^{\phi1})^2 \cdot (t_{i2}^{\phi2})^2 \cdot T_{\omega_1+\omega_2}^S \cdot W_{i1} \cdot W_{i2} \frac{\sin^2(\Psi_{SFG}^{\phi1\phi2 \to S}(\alpha))}{[n_{i1}^{\phi1}(\omega_1) \cdot n_{i2}^{\phi2}(\omega_2) - n_{u3}^S(\omega_1+\omega_2)^2]^2}$$

$$K^P = \left(\frac{512\pi^3}{A_1 * A_2}\right) \cdot (t_{i1}^{\phi1})^2 \cdot (t_{i2}^{\phi2})^2 \cdot T_{\omega_1+\omega_2}^P \cdot W_{i1} \cdot W_{i2} \frac{\sin^2(\Psi_{SFG}^{\phi1\phi2 \to P}(\alpha))}{[n_{i1}^{\phi1}(\omega_1) \cdot n_{i2}^{\phi2}(\omega_2) - n_{u3}^P(\omega_1+\omega_2)^2]^2}$$

where:
   $A_1$ and $A_2$ are transverse areas defined by intersections of said first and second optical signals ($s_{i1}, s_{i2}$) with a surface of the specimen;
   $t_{i1}^{\phi1}$ and $t_{i2}^{\phi2}$ are Fresnel transmission coefficients corresponding, respectively, to said first and second optical signals;
   $T_{\omega_1+\omega_2}^S$ and $T_{\omega_1+\omega_2}^P$ are Fresnel transmission coefficients corresponding, respectively, to said first and second orthogonal components of the sum optical signal ($s_{u3}$);
   the product $W_{i1} * W_{i2}$ is said power parameter;
   $n_{i1}^{\phi1}(\omega_1)$ and $n_{i2}^{\phi2}(\omega_2)$ are refractive indices of said material, respectively corresponding to said first optical signal and said second optical signal;
   $n_{u3}^S(\omega_1+\omega_2)$ and $n_{u3}^P(\omega_1+\omega_2)$ are refractive indices of said material, respectively corresponding to said first orthogonal component and said second orthogonal component of said sum optical signal;

$\Psi_{SFG}^{\phi1\phi2 \to S}(\alpha)$ and $\Psi_{SFG}^{\phi1\phi2 \to P}(\alpha)$ are phase factors, which have, respectively, the following expressions:

$$\Psi_{SFG}^{\phi1\phi2 \to S}(\alpha) = \left(\frac{\pi L}{2}\right)\left(\frac{2}{\lambda}\right)[n_{i1}^{\phi1}(\omega_1) \cdot \cos(\alpha_{r1}) + n_{i2}^{\phi2}(\omega_2) \cdot \cos(\alpha_{r2}) - 2n_{u3}^S(\omega_1+\omega_2) \cdot \cos(\alpha_{r3})]$$

$$\Psi_{SFG}^{\phi1\phi2 \to P}(\alpha) = \left(\frac{\pi L}{2}\right)\left(\frac{2}{\lambda}\right)[n_{i1}^{\phi1}(\omega_1) \cdot \cos(\alpha_{r1}) + n_{i2}^{\phi2}(\omega_2) \cdot \cos(\alpha_{r2}) - 2n_{u3}^P(\omega_1+\omega_2) \cdot \cos(\alpha_{r3})]$$

where L is a thickness of said material, $\lambda$ is a wavelength, $\alpha_{r1}$ and $\alpha_{r2}$ are said angles of refraction of the first and second optical signals $s_{i1}$ and $s_{i2}$, and $\alpha_{r3}$ is an angle formed by the sum optical signal $s_{u3}$ with said normal n.

13. The method according to claim 9, wherein providing a specimen comprises providing a specimen made at least in part of a material having a crystalline structure belonging to the 6mm crystalline class, wherein said number of sets of measurements comprises:
   a first set, which is associated to said first orthogonal component;
   a second set, which is associated to said second orthogonal component and in which said respective number of pairs of respective values comprises pairs of values such that said second polarization angle ($\phi_2$) is zero;
   a third set, which is associated to said second orthogonal component and the values of configuration of which are such that said angle of inclination ($\alpha$) is zero; and
   a fourth set, which is associated to said second orthogonal component;
and wherein said step of applying the method of numeric fitting comprises applying the method of numeric fitting to said first set, second set, third set, and fourth set, respectively, on the basis of a first parametric function, a second parametric function, a third parametric function, and a fourth parametric function, which have, respectively, the following expressions:

$$W_{u3}^S(\alpha) = K^S \cdot (d_{\mathit{eff}}^{\phi1\phi2 \to S}(\alpha))^2$$

$$W_{u3}^S(\alpha) = K^S \cdot (d_{\mathit{eff}\_1}^{\phi1\phi2 \to S}(\alpha))^2$$

$$W_{u3}^S(\alpha) = K^S \cdot (d_{\mathit{eff}\_2}^{\phi1\phi2 \to S}(\alpha))^2$$

$$W_{u3}^S(\alpha) = K^S \cdot (d_{\mathit{eff}\_3}^{\phi1\phi2 \to S}(\alpha))^2$$

where $K^S$ and $K^P$ are a first proportionality function and a second proportionality function, and where:

$$d_{\mathit{eff}}^{\phi1\phi2 \to S}(\alpha) = -d_{15}(\sin(\phi_1)\cos(\phi_2)\sin(\alpha_{r2}) + \cos(\phi_1)\sin(\alpha_{r1})\sin(\phi_2))$$

$$d_{\mathit{eff}\_1}^{\phi1\phi2 \to P}(\alpha) = -d_{31}\sin(\alpha_{r3})\sin(\phi_1)\sin(\phi_2$$

$$d_{\mathit{eff}\_2}^{\phi1\phi2 \to P}(\alpha) = -d_{24}\cos(\phi_1)\cos(\phi_2)[\cos(\alpha_{r1})\sin(\alpha_{r2}) + \sin(\alpha_{r1})\cos(\alpha_{r2})]$$

$$d_{\mathit{eff}\_3}^{\phi1\phi2 \to P}(\alpha) = -d_{24}\cos(\alpha_{r3})\cos(\phi_1)\cos(\phi_2)[\cos(\alpha_{r1})\sin(\alpha_{r2}) + \sin(\alpha_{r1})\cos(\alpha_{r2})] + -d_{31}\sin(\alpha_{r3})\sin(\phi_1)\sin(\phi_2) - d_{32}\sin(\alpha_{r3})\cos(\phi_1)\cos(\alpha_{r1})\cos(\phi_2)\cos(\alpha_{r2}) + -d_{33}\sin(\alpha_{r3})\cos(\phi_1)\sin(\alpha_{r1})\cos(\phi_2)\sin(\alpha_{r2})$$

where $\phi_1$ and $\phi_2$ are said first and second polarization angles, $\alpha_{r1}, \alpha_{r2}, \alpha_{r3}$ are angles of refraction corresponding, respectively, to said first and second optical signals ($s_{i1}, s_{i2}$), and to said sum optical signal ($s_{u3}$), and $d_{15}, d_{24}, d_{31}, d_{32}$ and $d_{33}$ are second-order nonlinear optical coefficients.

14. The method according to claim 9, wherein providing a specimen comprises providing a specimen made at least in part of a material having a crystalline structure belonging to the $\underline{4}3$ m crystalline class, wherein said number of sets of measurements comprises a first set, which is associated to said first orthogonal component, and wherein applying the numeric fitting comprises applying the numeric fitting to said first set, on the basis of a first parametric function, having the following expression:

$$W_{u3}^S(\alpha) = K^S \cdot (d_{\mathit{eff}}^{\phi1\phi2\rightarrow S}(\alpha))^2$$

where $K^S$ is a first proportionality function, and where:

$$\tilde{d}_{\mathit{eff}}^{\phi1\phi2\rightarrow S} = d_{14}\cos(\phi_1)\cos(\phi_2)[\cos(\alpha_{r1})\sin(\alpha_{r2}) + \sin(\alpha_{r1})\cos(\alpha_{r2})]$$

where $\phi_1$ and $\phi_2$ are said first and second polarization angles, $d_{14}$ is a second-order nonlinear optical coefficient, and $\alpha_{r1}$, $\alpha_{r2}$ are angles of refraction corresponding, respectively, to said first and second optical signals.

15. The method according to claim 14, wherein said number of sets of measurements further comprises:
a second set, which is associated to said second orthogonal component and the configuration values of which are such that said angle of inclination (a) is zero; and
a third set, which is associated to said second orthogonal component and the configuration values of which are such that said angle of inclination (a) is non-zero;
and wherein said step of applying the numeric fitting comprises applying the numeric fitting to said second and third sets, respectively, on the basis of a second parametric function and a third parametric function, which have, respectively, the following expressions:

$$W_{u3}^P(\alpha) = K^P \cdot (d_{\mathit{eff\_1}}^{\phi1\phi2\rightarrow P}(\alpha))^2$$

$$W_{u3}^P(\alpha) = K^P \cdot (d_{\mathit{eff\_2}}^{\phi1\phi2\rightarrow P}(\alpha))^2$$

where $K^P$ is a second proportionality function, and where:

$$\tilde{d}_{\mathit{eff}}^{\phi1\phi2\rightarrow P} = -d_{25}\{-\sin(\phi_1)\cos(\phi_2)\sin(\alpha_{r2}) - \sin(\phi_2)\cos(\phi_1)\sin(\alpha_{r1})\}$$

$$\tilde{d}_{\mathit{eff}}^{\phi1\phi2\rightarrow P} = -\cos(\alpha_{r3})d_{25}\{-\sin(\phi_1)\cos(\phi_2)\sin(\alpha_{r2}) - \sin(\phi_2)\cos(\phi_1)\sin(\alpha_{r1})\} + -\cos(\alpha_{r3})d_{36}\{-\sin(\phi_1)\cos(\phi_2)\cos(\alpha_{r2}) - \sin(\phi_2)\cos(\phi_1)\cos(\alpha_{r1})\}$$

where $\alpha_{r3}$ is an angle of refraction corresponding to said sum optical signal ($s_{u3}$), and $d_{25}$, $d_{36}$ are second-order nonlinear optical coefficients.

16. The method according to claim 9, wherein providing a specimen comprises providing a specimen made at least in part of a material having a crystalline structure belonging to the $\underline{3}$m crystalline class, wherein said number of sets of measurements comprises:
a first set, which is associated to said first orthogonal component and in which said respective number of pairs of respective values comprises pairs of values such that said first polarization angle ($\phi_1$) is equal to 90°;
a second set, which is associated to said first orthogonal component and in which said respective number of pairs of respective values comprises pairs of values such that said first polarization angle ($\phi_1$) is equal to 0°;
a third set, which is associated to said second orthogonal component and in which said respective number of pairs of respective values comprises pairs of values such that said first polarization angle ($\phi_1$) is equal to 90°;
a fourth set, which is associated to said second orthogonal component; and
wherein applying the numeric fitting comprises applying the numeric fitting to said first set, second set, third set, and fourth set, respectively on the basis of a first parametric function, a second parametric function, a third parametric function, and a fourth parametric function, which have, respectively, the following expressions:

$$W_{u3}^S(\alpha) = K^S \cdot (d_{\mathit{eff\_1}}^{\phi1\phi2\rightarrow S}(\alpha))^2$$

$$W_{u3}^S(\alpha) = K^S \cdot (d_{\mathit{eff\_2}}^{\phi1\phi2\rightarrow S}(\alpha))^2$$

$$W_{u3}^S(\alpha) = K^P \cdot (d_{\mathit{eff\_1}}^{\phi1\phi2\rightarrow S}(\alpha))^2$$

$$W_{u3}^S(\alpha) = K^P \cdot (d_{\mathit{eff\_2}}^{\phi1\phi2\rightarrow S}(\alpha))^2$$

where $K^S$ and $K^P$ are, respectively, a first proportionality function and a second proportionality function, and where:

$$\tilde{d}_{\mathit{eff\_1}}^{\phi1\phi2\rightarrow S} = d_{15}\{-\cos(\phi_2)\sin(\alpha_{r2})\} - d_{22}\{-\cos(\phi_2)\cos(\alpha_{r1})\}$$

$$\tilde{d}_{\mathit{eff\_2}}^{\phi1\phi2\rightarrow S} = d_{15}\{-\sin(\phi_2)\sin(\alpha_{r1})\} - d_{22}\{-\sin(\phi_2)\cos(\alpha_{r1})\}$$

$$\tilde{d}_{\mathit{eff\_1}}^{\phi1\phi2\rightarrow P} = \cos(\alpha_{r3})d_{22}[-\sin(\phi_2)] - \sin(\alpha_{r3})\{d_{31}[\sin(\phi_2)]\}$$

$$\tilde{d}_{\mathit{eff\_2}}^{\phi1\phi2\rightarrow P} = -\cos(\alpha_{r3})d_{22}[\cos(\phi_1)\cos(\alpha_{r1})\cos(\phi_2)\cos(\alpha_{r2}) - \sin(\phi_1)\sin(\phi_2)] + -\cos(\alpha_{r3})d_{15}\cos(\phi_1)\cos(\phi_2)[\cos(\alpha_{r1})\sin(\alpha_{r2}) + \sin(\alpha_{r1})\cos(\alpha_{r2})] + -\sin(\alpha_{r3})\{d_{31}[\cos(\alpha_1)\cos(\alpha_{r1})\cos(\phi_2)\cos(\alpha_{r2}) + \sin(\phi_1)\sin(\phi_2)] + d_{33}\cos(\phi_1)\sin(\alpha_{r1})\cos(\phi_2)\sin(\alpha_{r2})\}$$

where $\phi_1$ and $\phi_2$ are said first and second polarization angles, $\alpha_{i1}$, $\alpha_{r2}$, $\alpha_{r3}$ are angles of refraction corresponding, respectively, to said first optical signal ($s_{i1}$) and said second optical signal ($s_{i2}$), and to said sum optical signal ($s_{u3}$), and $d_{15}$, $d_{22}$, $d_{31}$ and $d_{33}$ are second-order nonlinear optical coefficients.

17. The method according to claim 9, wherein providing a specimen comprises providing a specimen made at least in part of a material having a crystalline structure belonging to the 32 crystalline class, and wherein said number of sets of measurements comprises:
a first set, which is associated to said first orthogonal component and in which said respective number of pairs of respective values comprises pairs of values such that said first polarization angle ($\phi_1$) is equal to 90°; and
a second set, which is associated to said second orthogonal component;
and wherein applying the numeric fitting comprises applying the numeric fitting to said first and second sets, respectively, on the basis of a first parametric function and a second parametric function, which have, respectively, the following expressions:

$$W_{u3}^S(\alpha) = K^S \cdot (d_{\mathit{eff}}^{\phi1\phi2\rightarrow S}(\alpha))^2$$

$$W_{u3}^P(\alpha) = K^P \cdot (d_{\mathit{eff}}^{\phi1\phi2\rightarrow P}(\alpha))^2$$

where $K^S$ and $K^P$ are, respectively, a first proportionality function and a second proportionality function, and where:

$$\tilde{d}_{\mathit{eff}}^{\phi1\phi2\rightarrow S} = d_{11}[\sin(\phi_2)]$$

$$\tilde{d}_{\mathit{eff}}^{\phi1\phi2\rightarrow P} = \cos(\alpha_{r3})d_{14}[-\sin(\phi_1)\cos(\phi_2)\sin(\alpha_{r2}) - \sin(\phi_2)\cos(\phi_1)\sin(\alpha_{r1})] + +\cos(\alpha_{r3})d_{11}[-\sin(\phi_1)\cos(\phi_2)\cos(\alpha_{r2}) - \sin(\phi_2)\cos(\phi_1)\cos(\alpha_{r1})]$$

where $\phi_1$ and $\phi_2$ are said first and second polarization angles, $d_{11}$ and $d_{14}$ are second-order nonlinear optical coefficients, and $\alpha_{r1}$ $\alpha_{r2}$, $\alpha_{r3}$ are angles of refraction corresponding, respectively, to said first optical signal ($s_{i1}$) and said second optical signal ($s_{i2}$), and to said sum optical signal ($s_{u3}$).

18. The method according to claim 5, wherein said numeric fitting is chosen from among: the least-squares method, the singular-value-decomposition method, the Monte Carlo method, the Tikhonov regularization method.

19. A system for determining second-order nonlinear optical coefficients of a non-centrosymmetrical material forming at least in part a specimen, comprising:
   a support mechanism configured for carrying said specimen,
   an optical-generator configured for generating a first optical signal and a second optical signal, respectively with a first pulsation and a second pulsation, and with a first polarization state and a second polarization state, said optical-generator and said support mechanism being arranged in such a way that said first and second optical signals impinge upon said specimen in such a way that said specimen generates a sum optical signal with a third pulsation and a third polarization state, said third pulsation being equal to the sum of said first and second pulsations, said third polarization state being a function of said first and second polarization states, said optical-generator being further configured in such a way that said first and second optical signals impinge upon said specimen with linear polarizations in such a way that said sum optical signal is linearly polarized, said first and second polarization states being defined, respectively, by a first polarization angle and a second polarization angle;
   a power measurement device to measure the power, configured for determining a plurality of measurements of power corresponding to said sum optical signal, and
   a processor configured for determining said second-order nonlinear optical coefficients on the basis of said plurality of measurements;
   wherein said optical-generator is controllable so as to vary said first and second polarization angles at each power measurement, in such a way that they assume a plurality of pairs of respective values, said values being comprised in a range with a width of at least 180°.

20. The system according to claim 19, wherein said optical-generator is controllable to vary said first and second polarization angles in the ranges between [−180°;180°] and [0°; 180°], respectively.

21. The system according to claim 20, wherein said optical-generator includes a first and a second half-wave plate.

22. The system according to claim 21, wherein said processor is further configured for executing a numeric fitting on at least one set of measurements of power of said plurality, on the basis of at least one parametric function, said parametric function having as parameters at least one of said second-order nonlinear optical coefficients.

* * * * *